US007374905B2

(12) United States Patent
Copeland et al.

(10) Patent No.: US 7,374,905 B2
(45) Date of Patent: May 20, 2008

(54) MEDIUM COMPOSITION, METHOD AND DEVICE FOR SELECTIVELY ENHANCING THE ISOLATION OF ANAEROBIC MICROORGANISMS CONTAINED IN A MIXED SAMPLE WITH FACULTATIVE MICROORGANISMS

(75) Inventors: James C. Copeland, Ashland, OH (US); Kathy J. Myers, Mansfield, OH (US)

(73) Assignee: Oxyrase, Inc., Mansfield, OH (US)

(*) Notice: Subject to any disclaimer, the term of this patent is extended or adjusted under 35 U.S.C. 154(b) by 5 days.

(21) Appl. No.: 10/007,739

(22) Filed: Nov. 8, 2001

(65) Prior Publication Data

US 2003/0138867 A1 Jul. 24, 2003

Related U.S. Application Data

(60) Provisional application No. 60/246,872, filed on Nov. 8, 2000.

(51) Int. Cl.
*G01N 33/554* (2006.01)
*G01N 33/569* (2006.01)
*C12Q 1/04* (2006.01)

(52) U.S. Cl. .......................... 435/34; 435/7.32; 435/30; 435/38; 435/29; 435/404; 435/307.1; 435/308.1

(58) Field of Classification Search .................. 435/4, 435/15, 18, 25, 26, 139, 800, 262, 21, 31, 435/32, 34, 7.32, 283.1, 287.1, 288.3, 288.4, 435/289.1, 305.1, 305.2, 305.3, 39, 254.2, 435/168, 173.1, 173.9, 244, 257.1, 257.6; 195/103.5; 210/632, 717, 721, 759, 909; 438/253; 530/300
See application file for complete search history.

(56) References Cited

U.S. PATENT DOCUMENTS 2,348,448 A 5/1944 Brewer (Continued)

FOREIGN PATENT DOCUMENTS

EP 0427813 * 5/1994

(Continued)

OTHER PUBLICATIONS

Jones, MV et al, Jouranl of general microbiology, vol. 130(1), pp. 95-101, Temperature dependent azide sensitivity of growth and ATPase activity in the facultative thermophile, *Bacillus coagulans*.*

(Continued)

*Primary Examiner*—Mark Navarro
*Assistant Examiner*—Ginny Allen Portner
(74) *Attorney, Agent, or Firm*—Fay Sharpe LLP

(57) ABSTRACT

The present invention is directed to a medium, broth or agar, and a method of utilizing the same, in order to isolate and/or identify anaerobes from a mixed sample that contains facultative microorganisms. The medium contains an inhibitor of the electron transport system, such as a salt of azide ($N_3^-$), cyanide ($CN^-$) or related compounds. These inhibitors are present in an amount sufficient to limit the growth of facultative microorganisms under anaerobic conditions while not inhibiting the growth of the anaerobe microorganisms. Preferably, the inhibitor is present in the amount of from about 0.1 mg/ml to about 1.0 mg/ml in broth medium, and from about 0.01 mg/ml to 1.0 mg/ml in agar medium.

26 Claims, 15 Drawing Sheets

U.S. PATENT DOCUMENTS

| | | | |
|---|---|---|---|
| 3,198,713 A | | 8/1965 | McCormick |
| 3,721,607 A | * | 3/1973 | Gruber et al. ............... 435/14 |
| 3,767,790 A | | 10/1973 | Guttag |
| 4,029,546 A | | 6/1977 | Brouillard |
| 4,040,908 A | * | 8/1977 | Clark, Jr. .................. 205/778 |
| 4,078,971 A | | 3/1978 | Arkles et al. |
| 4,091,116 A | | 5/1978 | Edwards et al. |
| 4,195,129 A | | 3/1980 | Fukui et al. |
| 4,242,461 A | | 12/1980 | Bartoli et al. |
| 4,254,220 A | * | 3/1981 | Meiattini .................... 435/14 |
| 4,414,334 A | * | 11/1983 | Hitzman .................... 435/262 |
| 4,430,427 A | * | 2/1984 | Hopkins ..................... 435/25 |
| 4,476,224 A | * | 10/1984 | Adler ..................... 435/253.6 |
| 4,485,016 A | * | 11/1984 | Hopkins ..................... 210/632 |
| 4,501,674 A | | 2/1985 | Wu |
| 4,528,199 A | * | 7/1985 | Moon et al. .................. 426/53 |
| 4,602,987 A | | 7/1986 | Bonaventura et al. |
| 4,708,796 A | | 11/1987 | Yoshimoto et al. |
| 4,791,061 A | | 12/1988 | Sumino et al. |
| 4,808,517 A | * | 2/1989 | Blondin et al. ............... 435/4 |
| 4,810,633 A | * | 3/1989 | Bauer et al. .................. 435/25 |
| 4,882,280 A | * | 11/1989 | Takashio et al. ............ 435/228 |
| 4,894,339 A | * | 1/1990 | Hanazato et al. ........... 435/182 |
| 4,954,354 A | | 9/1990 | Hopkins et al. |
| 4,996,073 A | | 2/1991 | Copeland et al. |
| 5,034,331 A | | 7/1991 | Brewer |
| 5,081,015 A | * | 1/1992 | Hayashi et al. .......... 205/777.5 |
| 5,106,633 A | | 4/1992 | Edens et al. |
| 5,223,291 A | | 6/1993 | Levinson et al. |
| 5,240,853 A | | 8/1993 | Copeland et al. |
| 5,272,083 A | | 12/1993 | Butz et al. |
| 5,362,501 A | | 11/1994 | Gopeland et al. |
| 5,405,773 A | * | 4/1995 | Fung et al. .................. 435/243 |
| 5,482,860 A | * | 1/1996 | Copeland et al. ......... 435/293.1 |
| 5,498,528 A | * | 3/1996 | King ............................ 435/34 |
| 5,789,191 A | * | 8/1998 | Mayer et al. .................. 435/39 |
| 5,830,746 A | * | 11/1998 | Copeland et al. ........... 435/243 |
| 5,871,952 A | * | 2/1999 | Ghirardi et al. ............... 435/34 |
| 5,955,344 A | * | 9/1999 | Copeland et al. ........... 435/243 |
| 6,087,358 A | * | 7/2000 | Baker et al. ............. 514/230.5 |
| 6,153,400 A | * | 11/2000 | Matsumura et al. .......... 435/32 |
| 6,204,051 B1 | * | 3/2001 | Copeland et al. ......... 435/305.4 |
| 6,376,211 B1 | * | 4/2002 | Little, II et al. .............. 435/21 |
| 6,429,008 B1 | * | 8/2002 | Copeland et al. ......... 435/303.2 |
| 6,485,947 B1 | * | 11/2002 | Rajgarhia et al. ........... 435/139 |
| 7,018,828 B1 | * | 3/2006 | Taintor .................... 435/253.6 |
| 2002/0045245 A1 | * | 4/2002 | Copeland et al. ......... 435/305.3 |
| 2003/0124643 A1 | * | 7/2003 | Taintor ........................ 435/40 |
| 2003/0138874 A1 | * | 7/2003 | Taintor ........................ 435/34 |

FOREIGN PATENT DOCUMENTS

| | | | |
|---|---|---|---|
| WO | 88/04319 | * | 6/1988 |
| WO | 92/07088 | * | 4/1992 |

OTHER PUBLICATIONS

Kone, K et al, Abstracts of the General Meeting of the American Society for Microbiology, vol. 94(0), p. 372, abstract No. P-20,May 23-27, 1994.*

Merad, AS et al, Archives Institut Pasteur d'Algerie (Algeria), 1992, vol. 58, pp. 161-168, Efficiency of inhibitors (phenylethanol, nalidixic acid, sodium azide) in the isolation of strictly anaerobic bacteria from a polymicrobial specimen, English abs.*

Pratt, K et al, 92nd General Meeting of the American Society of Microbiology, New Orleans, Louisianna, USA, May 26-30, 1992, Abstr. Gen. Meet. Am. Soc. Microbiol. vol. 92(0), 1992, p. 481, abstract C-366.*

Spangler, SK et al, J. Clin. Microbiology, vol. 33(5), pp. 1366-1367, May 1995, Susceptibilities of 201 anaerobics to erythromycin, azithromycin, clarithromycin and roxithromycin by oxyrase agar dilution and E-test methodologies.*

Tillonen, J et al, Clinical and experimental research, vol. 22(5), Aug. 1998.*

Wiggs, LS et al, J. Clinical Microbiology, vol. 38(2), pp. 499-507, Feb. 2000.*

Wong, PCK, Abstracts of the General Meeting of the American Society for Microbiology, vol. 97(0), p. 448, abstract P-73, May 1997.*

English translation for Merad et al, 1992, The efficacy of inhibitors in the isolation of strict anaerobic bacteria from a polymicrobial sample, Laboratoire des Anaerobies, Institut Pasteur, Arch. Inst. Pasteur Algerie, vol. 58, p. 161-168.*

Asperger, H et al, A comparison study between Oxyrase anaerobic agar plates and conventional anaerobic method for the enumberation of lactic acid and bifidobacteria from fermented milk. Milchwissenschaft, vol. 45(110, p. 613-616, 1999.*

Merad et al (English translation) The efficacy of inhibitors in the isolation of strict anaerobic bacteria, 1992, reference of record.*

Hope, KM et al, FEMS Microbiol. Lett. May 15, 1991, vol. 64(2-3), apges 217-220, The anaerobic utilization of cyanide in the presence of sugars by microbiol cultures can involve an abiotic process (abstract only).*

Milgrom, Ya.M. et al, Catalytic properties of the membrane bound ATPase of Anaerobic bacterium *Lactobacillus casei*, English Abstract, Biologicheskie Membrany (Moscow), vol. 5(6), pp. 565-572, 1988 (Russian article, English abstract last page).*

Tarakhovsku, Yu. S. et al, Dynamics of changes in the ultrastructur of *Escherichia coli* membranes during plasmolysis, Biologicheskie Membrany (Moscow) vol. 6(5), pp. 530-540, 1989, (Russian article, English abstract last page).*

Tillonen, J et al, Alcoholism: Clinical and Experimental Research, vol. 22(5), Aug. 1998, Role of Catalase in In vitro acetaldyhde formation by human colonic contents, pp. 1113-1119.*

Wiggs, Lois S et al, Journal of Clinical Microbiology, Feb. 2000, vol. 38(2), pp. 499-507, Evaluation of the Oxyrase OxyPlate anaerobe incubation system.*

Sjogren, R.E. et al, App Environ, Microb., vol. 41(6), Jun. 1981, p. 1931-1936 Bacterial Survival in a dilute Environment.*

Howell, BJ et al, The Journal of Cell Biology, vol. 150(6), Sep. 18, 2000, pp. 1233-1249.*

Midley, M et al, Biochem. J. 1973, vol. 132, pgaes 141-154.*

Tillonen, J et al, Alcohol Clin. Exp. Res, Aug. 1998, vol. 22(5), pp. 1113-1119 (abstract only).*

Underground Tank Technology Update, vol. 12(2), Mar./Apr. 1998, Laboratory Study of BTEX biodegradation, pp. 2-16.*

Oxyrase, Inc. EC Oxyrase Enzyme System Product inert.*

Merad et al , reference of record.*

Tarakhovsk et al, reference of record (english abstract).*

Milgrom et al, reference of record (english abstract).*

* cited by examiner

MEDIUM COMPOSITION, METHOD AND DEVICE FOR SELECTIVELY ENHANCING THE ISOLATION OF ANAEROBIC MICROORGANISMS CONTAINED IN A MIXED SAMPLE WITH FACULTATIVE MICROORGANISMS

The present application claims the benefit of priority to U.S. Provisional Application Ser. No. 60/246,872 filed on Nov. 8, 2000.

FIELD OF THE INVENTION

The present invention is directed to the field of microbiology, and in particular to compositions, processes and devices for isolating and/or identifying anaerobic microorganisms.

BACKGROUND OF THE INVENTION

Anaerobic microorganisms are organisms which have the ability to grow in the absence of oxygen. The term, anaerobe, is commonly reserved for those organisms which, in nature, normally grow in (or, in the case of obligatory or strict anaerobes, can only grow in) anaerobic habitats. These are environments in which oxygen is absent. The anaerobes lack the ability to synthesize an oxygen-linked respiratory chain and must, therefore utilize alternate energy-yielding metabolism processes, such as fermentation, photosynthesis, etc.

Some anaerobic-like microorganisms can also grow under aerobic conditions. These are called facultative anaerobes or microbes as opposed to strict or obligatory anaerobes. In essence, these organisms generally prefer an oxygen environment but are capable of living and growing in its absence. Consequently, facultative microbes are capable of growing and/or surviving in the presence or absence of molecular oxygen.

Anaerobe microorganisms are economically important in health care, in food industry, and in the environment. However, anaerobes are difficult to isolate and grow because of their requirement for anaerobiosis and a chemically reduced state. To achieve these conditions requires specially prepared media to produce the reduced state and devices to create and maintain an oxygen free environment. The techniques that are required to use these devices add time and cost to working with anaerobes. New approaches, such as use of biocatalytic oxygen reducing agents, see for example the Oxyrase® microbiological products and processes, (U.S. Pat. Nos. 4,476,224; 4,996,073; 5,240,853; 5,432,083; 5,362,501; and 5,482,860) and specially design Petri dishes or culture plates, such as OxyDish™, (U.S. Pat. Nos. 5,830,746 and 5,955,344) of Oxyrase, Inc., Mansfield, Ohio (the assignee of the present invention), have simplified and reduced costs for isolating and growing these important microbes. The above mentioned patents are included herein by reference.

However, the very nature of anaerobes and the places that they are found conspire to make their isolation difficult. Because anaerobes lack respiratory enzymes for utilizing oxygen, they derive less energy from substrates than do facultative microbes, that have these enzymes. That means when anaerobes grow together with facultative microbes, some facultative microbes grow faster and more efficiently than do the anaerobes.

Furthermore, the majority of clinical specimens (80% to 85%) are mixed with both anaerobe and facultative microbes. Samples taken from food and from the environment often contain mixed cultures. If grown together, the facultative microbes often out grow the anaerobes, resulting in a diminution of the anaerobe numbers relative to the facultative microbes.

Additionally, when a specimen is spread onto a plate for isolated colonies, often the number of individual colonies obtained is about 100 or less. If the ratio of anaerobe to facultative falls to about 1%, the isolation of the anaerobe on a plate may be missed.

The crowding of facultative microbes and the presence of a relatively infrequent anaerobe on the same plate makes isolation of the anaerobe in pure form difficult. Not only is the anaerobe colony difficult to find, but it is often located in a crowded field that makes picking the colony difficult to do.

To be able to efficiently isolate a pathogenic anaerobe from among a mixed flora in a clinical specimen is important to the patient and can impact the cost of health care associated with treating that patient. The time it takes to recognize the presence of an anaerobe in a food sample is important to public health issues and to the economics of food packaging, storage, and shipment.

The object of this invention is to provide a medium (or a medium composition), process and/or device that retards or restricts the growth of facultative microbes, but not that of anaerobe microbes. The medium composition comprises a nutrient medium, an oxygen reducing agent (preferably, biocatalytic) and a cyanide, azide, and/or other related inhibitor compounds. These compounds act by chemically, irreversibly bonding to key enzymes or factors in the respiratory chain, thereby disabling them from handling oxygen. Such selective use of inhibitors restricts the growth of facultative microbes and removes the relative advantage that facultative microbes have when competing with anaerobe microbes.

Accordingly, it is an object of the present invention to provide an improved media composition, method and/or device for isolating and/or identifying anaerobic microorganisms contained in a mixed culture sample with facultative microorganisms.

These and other objects and features of the invention will be apparent from the following summary and description of the invention and from the claims.

SUMMARY OF THE INVENTION

The present invention addresses all of the foregoing objectives and provides a medium composition, method and device for the rapid recognition, isolation and identification of anaerobes from samples that contain facultative microorganisms.

In one aspect, the present invention is directed to a medium, broth or agar, and a method of utilizing the same, in order to isolate and/or identify anaerobes from a mixed sample that contains facultative microorganisms. The medium contains an inhibitor of the electron transport system, such as a salt of azide ($N_3^-$), cyanide ($CN^-$) or related compounds. These inhibitors are present in an amount sufficient to limit the growth of facultative microorganisms under anaerobic conditions while not inhibiting the growth of the anaerobe microorganisms. Preferably, the inhibitor is present in the amount of from about 0.1 mg/ml to about 1.0 mg/ml in broth medium, and from about 0.01 mg/ml to 1.0 mg/ml in agar medium.

In another aspect, the invention relates to a method for the rapid recognition, isolation, or identification of anaerobes from mixed samples that also contain facultative microorganisms comprising the following steps:

a. providing a medium composition comprising a nutrient medium and a salt of an azide, wherein the azide is present in an amount sufficient to limit the growth of facultative microorganisms while not limiting the growth of anaerobic organisms;

b. inoculating a sample into the medium composition;

c. incubating the inoculated medium composition anaerobically;

d. comparing growth in the medium composition, with partial growth with the azide being indicative that an anaerobe is present; and, e. sampling the medium composition containing the azide for further characterization and isolation of the anaerobe organism.

In a further aspect, the invention is directed to a device for the transport of a sample that contains anaerobes and facultative microbes to enable the recovery of the anaerobes, wherein the device comprises:

a. a medium composition comprising limited nutrients such as salts or buffers, liquid or solid, and an effective concentration of a salt of azide; and, b. a means for creating an anaerobic environment for the medium composition.

In a still another aspect, the invention concerns a medium composition which allows for the selective growth of anaerobic microbes contained in a mixed sample also containing facultative microbes. The medium composition comprises a microbiological nutrient medium containing a hydrogen donating substance, a plurality of oxygen scavenging membrane fragments which contain an electron transport system which reduces oxygen to water in the presence of a hydrogen donor, and an inhibitor of the electron transport system required for cellular respiration, wherein the inhibitor is present in an amount sufficient to limit the growth of facultative microbes while not limiting the growth of anaerobic microbes. Preferably, the oxygen scavenging membrane fragments are derived from the cytoplasmic membranes of bacteria or they are derived from membranes of mitochondrial organelles.

In a still further aspect, the present invention is directed to a medium composition which restricts the growth of facultative microbes but not anaerobic microbes comprising a nutrient medium containing a hydrogen donating organic substrate, one or more oxygen scavenging membrane fragments derived from the cytoplasmic membranes of bacteria or from the membranes of mitochondrial organelles of non-bacterial organisms, and an inhibitor of the electron transport system required for aerobic respiration.

In an additional aspect, the invention relates to a method for the selective growth and isolation of an anaerobe from a mixed sample also containing a facultative microbe, said method comprising the steps of:

a. providing a medium composition comprising a nutrient medium containing a hydrogen donating substance, oxygen scavenging membrane fragments which contain an electron transport system which reduces oxygen to water in the presence of a hydrogen donor, and an inhibitor of the electron transport system required for respiration, wherein the inhibitor is present in an amount sufficient to limit the growth of the facultative microbe but not of the anaerobes;

b. inoculating the medium composition with the mixed sample; and, c. incubating the medium composition containing the mixed sample under anaerobic conditions.

The foregoing has outlined some of the most pertinent objects of the invention. These objects should be construed to be merely illustrative of some of the more prominent features and applications of the intended invention. Many other beneficial results can be attained by applying the disclosed invention in a different manner or by modifying the invention within the scope of the disclosure. Accordingly, other objects and a more detailed understanding of the invention may be had by referring to the drawings, the detailed description of the invention and the claims which follow below.

BRIEF DESCRIPTION OF THE DRAWINGS

The following is a brief description of the drawings which are presented for the purposes of illustrating the invention and not for purposes of limiting the same.

Figure 1:
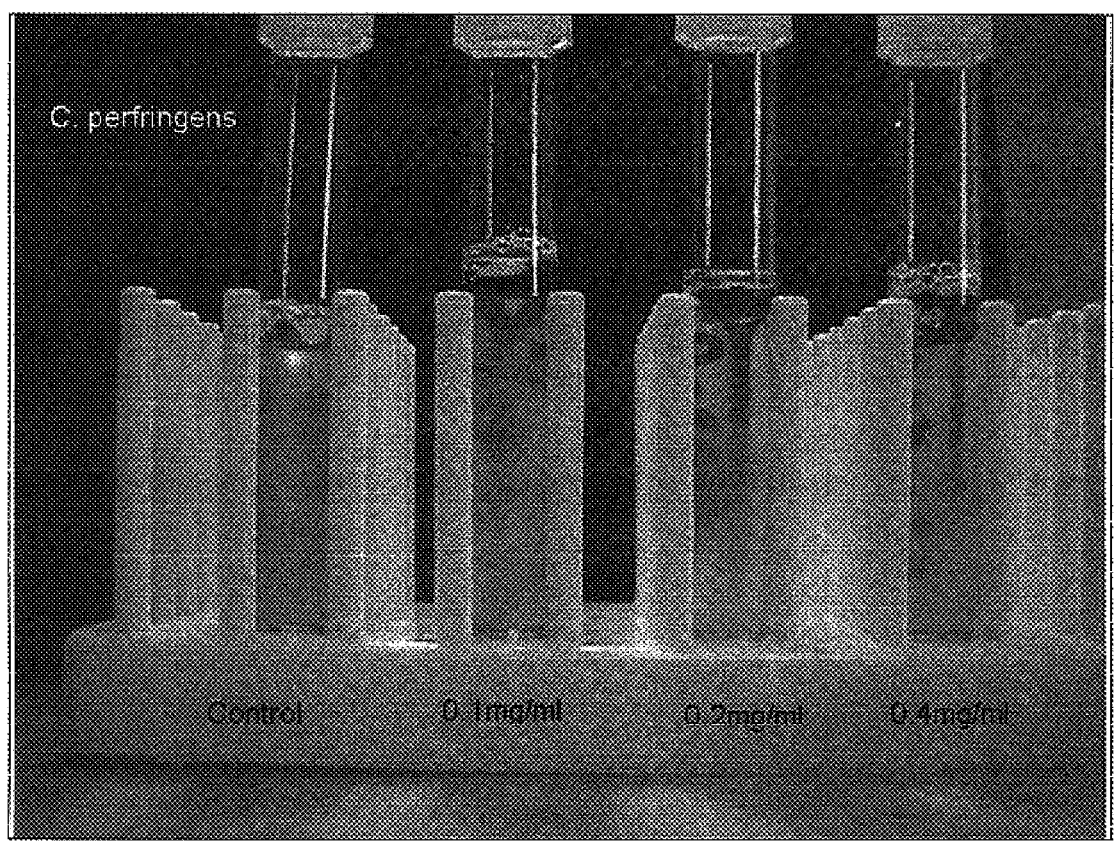
FIG. 1 is a photograph showing the growth of *C. perfringens* at various azide concentrations.

FIG. 3 is a photograph showing the growth of *E. coli* at various azide concentrations.

FIG. 4 is a photograph showing the growth of *P. mirabilis* at various azide concentrations.

FIG. 5 is a photograph comparing the growth of *B. fragilis* on culture plates containing ("AnaSelect OxyPlate™") or lacking ("Brucella OxyPlate ™") azide.

FIG. 6 is a photograph comparing the growth of *C. perfringens* on culture plates containing ("AnaSelect OxyPlate™") or lacking ("Brucella OxyPlate™") azide.

FIG. 7 is a photograph comparing the growth of *P. levii* on culture plates containing ("AnaSelect OxyPlate™") or lacking ("Brucella OxyPlate™") azide.

FIG. 8 is a photograph comparing the growth of *D. anaerobius* on culture plates containing ("AnaSelect OxyPlate™") or lacking ("Brucella OxyPlate™") azide.

FIG. 9 is a photograph comparing the growth of *F. nucleatum* on culture plates containing ("AnaSelect OxyPlate™") or lacking ("Brucella OxyPlate™") azide.

FIG. 10 is a photograph comparing the growth of *E. coli* on culture plates containing ("AnaSelect OxyPlate™") or lacking ("Brucella OxyPlate™") azide.

FIG. 11 is a photograph showing a growth of the anaerobe *B. fragilis* along with the facultative microbes *E. coli* and *P. mirabilis* in culture plates containing ("AnaSelect OxyPlate™") or lacking ("Brucella OxyPlate™") azide.

FIG. 12 is a photograph showing a growth of the anaerobe *P. anaerobius* along with the facultative microbes *E. coli* and *P. mirabilis* in culture plates containing ("AnaSelect OxyPlate™") or lacking ("Brucella OxyPlate™") azide.

FIG. 13 is a photograph showing a growth of the anaerobe *P. levii* along with the facultative microbes *E. coli* and *P. mirabilis* in culture plates containing ("AnaSelect OxyPlate™") or lacking ("Brucella OxyPlate™") azide.

FIG. 14 is a photograph showing a growth of the anaerobe *F. nucleatum* along with the facultative microbes *E. coli* and *P. mirabilis* in culture plates containing ("AnaSelect OxyPlate™") or lacking ("Brucella OxyPlate™") azide.

FIG. 15 is a photograph showing a growth of the anaerobe *C. perfringens* along with the facultative microbes *E. coli* and *P. mirabilis* in culture plates containing ("AnaSelect OxyPlate™") or lacking ("Brucella OxyPlate™") azide.

DETAILED DESCRIPTION OF THE PREFERRED EMBODIMENTS OF THE INVENTION

The present invention relates to a liquid or solid medium composition for the selective enhancement of growth of anaerobes from a mixed sample also containing facultative microorganisms. The sample may be obtained from patients, animals (particularly economically important animals such as livestock), food, pharmaceutical or environmental sources. The medium composition comprises a nutrient medium, optionally an oxygen reducing agent (preferably a biocatalytic oxygen reducing agent such as oxygen scavenging membrane fragments), and an inhibitor of the respiratory electron transport system, such as a salt of azide, cyanide or like compounds.

It was found that the inclusion of an inhibitor (or poison) that blocked the respiratory function completely stopped, or practically stopped, all growth of various facultative microbes under anaerobic conditions. This is while at the same time growth of anaerobes were relatively unaffected.

This discovery was then applied to biocatalytic oxygen reducing agents such as the Oxyrase® microbiological products. However, the inventors were not optimistic about the outcome since the essence of these agents are the respiratory enzymes that are inhibited by these poisons. In fact, the inventors found that growth of *Escherichia coli* under anaerobic conditions is completely inhibited, or nearly so, by these poisons. This is the microbe that is the source of the respiratory enzymes used in the oxygen scavenging membrane fragments found in the commercial Oxyrase® products. Unexpectedly, the inventors found that isolated respiratory enzymes bound to a membrane were resistant to the affect of these poisons or inhibitors at levels that limit or stop the growth of the intact microbe. This unexpected finding allowed the extension of this invention to that of certain anaerobic media containing biocatalytic oxygen reducing agents such as the oxygen scavenging membrane fragments found in the Oxyrase® microbial products.

Further the inventors found that even though growth of the facultative microbe could be stopped or greatly limited, the facultative microbe remained viable and would grow when then placed in or on a medium lacking the poison or inhibitor. This observation gave rise to another invention, that of a method to reduce the time to recognize the presence of an anaerobe and to significantly aid in the separation and isolation of the anaerobe from the facultative microbes present.

The first step of this method is to inoculate the specimen, or mixed culture, into an anoxic broth tube containing an effective concentration of the poison that will inhibit or greatly retard the growth of the facultative microbes while leaving the anaerobe microbes unaffected. The second step is to use the enriched broth culture to inoculate plated media that contains an effective concentration of the poison and to incubate the plate under anaerobic conditions. The first step amplifies the anaerobes present, which leads to their recognition and aids in their identity. The second step provides isolated colonies of the anaerobe free of facultative microbes that make possible purification and characterization of the anaerobe microbe.

The presence of an anaerobe is detected in the first step of this method by comparing growth in a tube containing the poison to a tube lacking it. Growth in the tube with the poison is an indicator that an anaerobe microbe is present. A sample is then removed for microscopic observation and for testing by means of DNA probes, RNA probes, or specific antibodies to rapidly identify any target anaerobe present.

Plating the amplified anaerobe cells from the selective broth medium onto solid media containing the poison and incubating that plate anaerobically provides a means to obtain isolated colonies of the anaerobe free from facultative colonies. However, the inventors have found that facultative microbes may not grow or grow very little in the broth tube with poison under anoxic conditions, but they will remain viable. If plated onto an agar medium without poison, then the still numerous facultative cells grow and crowd the plate, making observation and isolation of the anaerobe colony difficult. Plating onto a plate containing the poison and incubating it anaerobically further limits facultative microbes which then allows for enhanced isolation of the anaerobe microbe.

The nutrient media utilized in the invention is any liquid or solid preparation suitable for the growth, maintenance, storage, differential, isolation and/or identification of microorganisms. These include those utilized for the initiation of a culture (or subculture), for enrichment, or for diagnostic (identification) tests of various organisms. These are tests in which the identity of a given organism may be deduced from the characteristics of its growth in or on particular media. Preferably, the nutrient media is particularly suitable for the growth, isolation and/or identification of anaerobes.

Solid medium usually consists of liquid medium which have been solidified (i.e. "gelled") with an agent such as agar or gelatin. The degree of solidification can also vary, with stiff agar being preferred to inhibit "swarming" and semi-solid or "sloppy" agar being used to observe other characteristics. Before utilization, such medium is preferably sterile.

Moreover, anaerobes require an oxygen-free gaseous above the surface of the medium and a medium free from dissolved oxygen. Even under these conditions, some anaerobes may not grow unless the medium has been pre-reduced, i.e. poised at or below a particular redox potential. Consequently, reducing agents, such as those containing sulphhydrl groups (e.g., $H_2S$, cysteine, thioglycollate) may also be included in the medium composition of the present inventors.

Examples of commonly available medium being suitable for use for the selective growth of anaerobes is in the present invention, include, but are not limited to, Brain Heart Infusion, Brucella, CDC Anaerobe, Nutrient, Schaedler, Thioglycollate or Trypticase Soy. These are in both broth or agar form.

Additionally, the medium may be made anaerobic in an anaerobic jar, chamber or bag. An anaerobic jar is a container used for the incubation of materials (e.g. inoculated media) in the absence of oxygen or, in general, under gaseous conditions other than atmospheric. These are commonly known under the designations "Brewer Jar", "Gaspak", "McIntosh and Filde's Anaerobic Jar", etc.

Alternatively, the medium may be made anaerobic through the use of biocatalytic oxygen reducing agents such as the Oxyrase® enzyme system available from Oxyrase, Inc. of Mansfield, Ohio. In this regard, "Oxyrase® for Agar" is a filtered enzyme additive used to produce anaerobic conditions in a wide variety of bacteriological agar medium. Similarly, "Oxyrase® for Broth" is an enzyme additive used to produce anaerobic environments in bacteriological broth medium. Both of these mediums (media) are commercially available in sterile (EC) and non-sterile (EC/NS)-form.

The above-identified biocatalytical oxygen reducing agents consists of an enzyme system derived from the cytoplasmic membranes of microorganisms such as *E. coli*. The commercially available agents consists of a buffered suspension of membrane particles, 0.2 microns or smaller. The enzyme system is active over wide pH and temperature ranges. The exact amount of membranes containing the enzyme systems needed to reduce oxygen in the medium varies by a number of parameters including pH, temperature, kinds and amounts of substrate present, surface to depth ratio of the container, and headspace volume. As understood by those skilled in the art, some experimentation may be necessary to optimize the effectiveness of the membranes.

The preferred biocatalytic oxygen reducing agent utilized in the invention is comprised of oxygen scavenging membrane fragments which contain an electron transport system which reduces oxygen to water in the presence of a hydrogen donor. These oxygen scavenging membrane fragments can be derived from the cytoplasmic membranes of bacteria and/or from the membranes of mitochondrial organelles of a large number of higher non-bacterial organisms. Other known biocatalytic oxygen reducing agents such as glucose oxidase, alcohol oxidase, catalase, etc. can also be supplemented or utilized in the present invention, although generally less preferably.

The biocatalytic oxygen reducing agents suitable for use in the invention are non-toxic to microorganisms. Being catalysts, they are dynamic and highly efficient at reducing the oxygen in a trapped headspace, such as in a specially designed culture dish, OxyDish™. The biocatalytic oxygen reducing agents use substrates that are commonly found in microbiological media and that are natural to microorganisms to effect this reaction. Optionally, hydrogen donating substances can be added to the media. The products produced from this reaction are also natural and non-toxic to microorganisms. The use of the biocatalytic oxygen reducing agents makes possible the opening and closing of this dish if necessary and continues to reduce the oxygen trapped in the headspace after each occurrence.

The culture dish ("OxyDish™") containing the oxygen reducing agent (see U.S. Pat. Nos. 5,830,746 and 5,955,344) provides a means to work with anaerobic microorganisms free of the complications and expense of anaerobic bags, jars, incubators, or chambers. Consequently, use of these culture dishes is preferred. Each dish is light in weight and is designed to be stacked without crushing the solid (agar or gelatin-based) medium in the lower dishes in the stack. The dishes can be made of low cost materials, preferably plastic, they are designed to be readily molded, they are sterilizable, and preferably they can be disposable after use. Because of the incorporation of a biocatalytic means of removing oxygen, an enlarged headspace is also optionally provided. This enlarged headspace relieves the difficulties produced by moisture condensation.

Moreover, the dish top of the OxyDish™ in certain embodiments, has a small dome or cavity designed to contain an anaerobic gas (such as $CO_2$) generating pad or indicator strips to show the anaerobic state within the headspace of the closed culture dish. A variation of this dish design provides for additional removal of moisture from the dish as needed by placing pores in the bottom of the dish base. This feature prevents the build-up of excess condensate inside the dish which leads to flooding of the agar media surface. The pores are too small to let molten agar media flow out of the dish, yet they provide an exit for moisture. Any oxygen intruding into the dish through these pores must pass through the media containing the oxygen reducing agent. This intruding oxygen is removed before it can diffuse to the top layer of media or into the headspace where it would interfere with growth of anaerobic microorganisms.

The "OxyDish™" is also designed for automated preparation of agar or gelatin-based media plates necessary for commercial production. When in the up-right position, the dish can be readily filled with molten medium (such as a molten agar or gelatin-based media) without the sealing ring contacting the medium surface. When stored or used, the dish is placed into an inverted position. In this position, a seal (i.e. a media-ring seal) is formed by the contact of the sealing ring of the dish top with the media surface contained in the dish bottom when the media surface comes to rest on the sealing ring. This creates a headspace defined by the media surface, the inside wall of the sealing ring, and the inside top of the dish lid.

Furthermore, when the culture dish is utilized with the oxygen reducing agent such as a biocatalytic oxygen reducing agent, the oxygen reducing agent in the media reacts with the oxygen trapped in that headspace. This reaction renders the headspace sufficiently low in oxygen such that microorganisms affected by the presence of oxygen can grow on the media surface typically within 24 to 48 hours when the dish is incubated at 35° C. to 37° C. in an aerobic incubator. Any oxygen that intrudes into the dish around the media-ring seal or through the plastic is removed by the action of the reducing agent. The catalytic reducing agent facilitates the design and function of this dish.

The preferred biocatalytic oxygen reducing agents suitable for use in the invention include the use of sterile membrane fragments derived from bacteria having membranes which contain an electron transport system which reduces oxygen to water in the presence of a hydrogen donor in the nutrient medium. It is known that a great number of bacteria have cytoplasmic membranes which contain the electron transport system that effectively reduces oxygen to water if a suitable hydrogen donor is present in the medium. Some of the bacterial sources include *Escherichia coli*, *Salmonella typhimurium*, *Gluconobacter oxydans*, and *Pseudomonas aeruginosa*. These bacterial membranes have been highly effective in removing oxygen from media and other aqueous and semi-solid environments.

The same oxygen reducing effects produces by the cell membrane fragments from the bacterial sources indicated above, are also present in the membrane of mitochondrial organelles of a large number of higher non-bacterial organisms. More particularly, a great number of fungi, yeasts, and plants and animals have mitochondria that reduces oxygen to water, if a suitable hydrogen donor is present in the medium. Some of the sources of oxygen reducing membranes from these mitochondria are: beef heart muscle, potato tuber, spinach, *Saccharomyces*, *Neurospora*, *Aspergillus*, *Euglena* and *Chlamydomonas*. The process of producing the useful mitochondrial membrane fragments involves the following steps:

1. Yeast, fungal cells, algae and protozoa, having mitochondrial membranes containing an electron transfer system which reduces oxygen to water, are grown under suitable conditions of active aeration and a temperature which is conducive to the growth of the cells, usually about 20° C. to 45° C. in a broth media. Alternately, mitochondria may be obtained from the cells of animal or plant origin.
2. The cells are collected by centrifugation or filtration, and are washed with distilled water.
3. For the preparation of crude mitochondrial membrane fragments, a concentrated suspension of the cells is treated to break up the cell walls and mitochondria.

This is accomplished by known means, for example, by ultrasonic treatment or by passing the suspension several times through a French pressure cell at 20,000 psi.
4. The cellular debris is removed by low speed centrifugation or by microfiltration (cross-flow filtration).
5. The supernatant or filtrate is subjected to high speed centrifugation (175,000×g at 5° C.) or ultrafiltration.
6. For the preparation of material of higher purity, the cells of step 2 are suspended in a buffer containing 1.0 M sucrose and are treated by means which break up the cell walls or membranes but leave the mitochondria intact. This is accomplished by known means, for example, by ultrasonic treatment, passage through a French pressure cell at low pressure, enzymatic digestion or high speed blending with glass beads.
7. The cellular debris from step 6 is removed by differential centrifugation or filtration.
8. The supernatant or retentate from step 7 is passed through a French Press at 20,000 psi to break the mitochondria into small pieces.
9. Mitochondria debris from step 7 is removed by centrifugation at 12,000×g for approximately 15 minutes or by microfiltration.
10. The supernatant or filtrate from step 9 is subjected to high speed centrifugation (175,000×g at 5° C.) or ultrafiltration.
11. The pellet or retentate from step 5 (crude mitochondrial fragments) or the pellet or retentate from step 10 (purified mitochondrial membrane fragments) are resuspended in a buffer solution at a pH of about 6.0 to about 8.0. A preferred buffer solution is 0.02 M solution of N-2-hydroxyethylpiperazine-N'-2-ethane sulfonic acid (HEPES).
12. The membrane fragments in the buffer solution are then passed under pressure through a filter having openings of about 0.2 microns.
13. The suspension is then stored at about −20° C. for later use or it may be freeze dried.

Furthermore, while many solidified medium do not require the addition of a hydrogen donor in order for the enzyme system present in the membrane fragments to reduce the oxygen present in the product to water, when synthetic medium or medium failing to contain a hydrogen donating substance are utilized, the addition of a hydrogen donor (i.e., an organic substrate) may be necessary in order for the membrane fragments to perform their oxygen removing functions. Suitable hydrogen donors are lactic acid, succinic acid, alpha-glycerol phosphate, formic acid, malic acid, and where available, their corresponding salts.

The present invention is further illustrated by the following examples. It is to be understood that the present invention is not limited to the examples, and various changes and modifications may be made in the invention without departing from the spirit and scope thereof.

A. Comparison of Broth Cultures with Azide

An initial test was done to determine if anaerobes would grow at azide concentrations that inhibited common facultative microbes. Azide ($N_3^-$) is an inhibitor of the electron transport system where it prevents the reduction of the oxidized $a_3$ component of cytochrome oxidase. In this regard, the sodium salt, $NaN_3$, has been found to be an inhibitor of electron transport which blocks electron flow from cytochrome oxidase to oxygen.

In this test, sodium azide was added to 5 ml Brain Heart Infusion ("BHI") broth tubes at a final concentration of 0.1 mg/ml. Oxyrase® for Broth consists of sterile membrane fragments obtained from *Escherichia coli*. To each tube was added Oxyrase® for Broth to create an anaerobic environment.

The tubes were then inoculated with stock cultures of a panel of anaerobes and facultative microbes as indicated below. The microbes *Escherichia coli* and *Proteus mirabilis* were chosen as representatives of facultative microbes because they are often encountered in clinical samples and are fast growing aggressive microbes that compete with anaerobe microbes. The broth was over-laid with sterile mineral oil to prevent oxygen from reentering the broth. The tubes were incubated at 37° C. for about 24 hours and the presence or absence of growth noted. A sample was removed from each tube and streaked onto a Brucella OxyPlate™, devoid of any azide which was incubated for three days at 37° C. before recording the results (See Table 1).

TABLE 1

Growth of Selected Anaerobes and Facultative Microbes in Broth Containing Azide

| Culture | Observation | OxyPlate ™ |
|---|---|---|
| Un-inoculated Control | No Turbidity | — |
| Anaerobe microbes | | |
| *Bacteriodes fragilis* | + + + + | + + + + |
| *Bifidobacterium adelocentis* | + + + + | + + + + |
| *Fusobacterium nucleatum* | + + + + | + + + + |
| *Porphyromonas levii* | No Turbidity | + |
| *Peptostreptococcus anaerobius* | + | − |
| Facultative microbes | | |
| *Escherichia coli* | No Turbidity | + + + |
| *Proteus mirabilis* | No Turbidity | + + + |

This preliminary experiment showed that at 0.1 mg/ml of azide in anoxic broth, most anaerobes grow whereas two commonly encountered facultative microbes did not grow. Furthermore, the results show that the azide did not inhibit the enzyme system found in Oxyrase® that was used to create the anaerobic environment. Also, even though visible growth was not present in the *P. levii* tube, the microbe grew as evidenced by colonies on the plate inoculated with this culture. Their was no explanation for the lack of growth of *P. anaerobius* on the plate in contrast to the obvious growth, albeit low, in the tube. Azide was bacteriostatic for the facultative microbes. Even though they did not grow in the presence of azide in anoxic broth, they retained their viability as determined by the numerous colonies on a plate inoculated with a sample from these tubes.

B. Assays of Oxyrase® with Azide

The preliminary experiment describe above had several unexpected outcomes. One was the sensitivity of *Escherichia coli* to azide while the Oxyrase® Enzyme System, which is obtained from *E. coli*, is insensitive to the same amount of azide. The inventors then set out to determine the affect of azide on the Oxyrase® Enzyme System. Three concentrations of azide (1.0 mg/ml, 0.1 mg/ml, and 0.01 mg/ml) were tested for its affect on Oxyrase activity as measured polargraphically with a Gilson Oxygraph. This instrument measures dissolved oxygen concentration and records it with time. Standard conditions used to measure Oxyrase® activity were chosen. An amount of Oxyrase® was mixed with the stated concentrations of sodium azide in tubes and incubated at 37° C. for up to 90 minutes. Samples were taken at 0 time, 45 minutes and 90 minutes of incubation. The activity of the Oxyrase® was determined with the Gilson Oxygraph and the results expressed in Oxyrase® units (See Table 2).

TABLE 2

Oxyrase Activity at Various Concentrations of Azide

| | Oxyrase Activity Azide Concentration | | |
|---|---|---|---|
| Time | 1.0 mg/ml | 0.1 mg/ml | 0.01 mg/ml |
| 0 min. | 115 u/ml | 115 u/ml | 115 u/ml |
| 45 min | 115 u/ml | 115 u/ml | 115 u/ml |
| 90 min | 115 u/ml | 115 u/ml | 115 u/ml |

These results clearly show that Oxyrase® activity is resistant to at least 10× the concentration of azide that inhibits growth of cells of *E. coli* under anaerobic conditions. Growth in anoxic broth was inhibited by 0.1 mg/ml of azide, and possibly less. These results show that the Oxyrase® Enzyme System can be used to generate anaerobic conditions in the presence of high concentrations of azide without any apparent effect on the activity of the enzyme system of the biocatalytic oxygen reducing agent of Oxyrase®.

C. Effectiveness of Azide in Agar Plated Media for Preferentially Inhibiting Facultative Microbes Isolation and purification of microorganisms is performed by streaking an inoculum of the microbe onto the surface of an agar plate and then picking isolated colonies that arise after incubation. These colonies are used for study of the pure culture. This is a basic technique that lies at the heart of the science of microbiology. The inventors found that azide could be used in anoxic broth to preferentially inhibit facultative microbes. Subsequently, the inventors sought to determine if this same effect would be observed on solid agar medium.

A series of test OxyPlates™ were made containing Brucella medium with Oxyrase® and different concentrations of sodium azide (0.01 mg/ml, 0.02 mg/ml, and 0.04 mg/ml). A drop of inoculum from a broth culture of stocks of microbes was streaked onto each plate. The plates were incubated 3 days at 37° C. and observed. The results are presented in Table 3.

TABLE 3

Growth of Select Anaerobe and Facultative Microbes on Azide Containing OxyPlate ™

| | Growth on Azide OxyPlate ™ Azide Concentration > | | | |
|---|---|---|---|---|
| | 0 mg/ml | 0.01 mg/ml | 0.02 mg/ml | 0.04 mg/ml |
| Anaerobe microbes | | | | |
| *Bacteriodes .fragilis* | + + + + | + + + + | + + + + | + + + + |
| *Clostridium perfringens* | + + + + | + + + + | + + + + | + + + + |
| *Fusobacterium nucleatum* | + + + | + + + | + + + | + + + |
| *Porphoramonas levii* | + + + + | + + + + | + + + + | + + + |
| *Peptostreptococcus anaerobius* | + + + + | + + + + | + + | + |
| Facultative microbes | | | | |
| *Escherichia coli* | + + + | + | +/− | − |
| *Proteus mirabilis* | + + + + | + + | + | − |

These results demonstrate that azide in agar with an anoxic environment produced by the oxygen scavenging membrane fragments has little if any impact on growth of anaerobe microbes, but has a significant adverse affect on the growth of facultative microbes. *P. mirabilis* is a very motile microbe and typically swarms on agar surfaces. This behavior complicates single colony isolation of other microbes on a plate with *P. mirabilis*. The inventors noted that under anoxic conditions and at concentrations of azide above 0.1 mg/ml and when *P. mirabilis* is diluted to isolated colonies, swarming is inhibited. This effect of azide provides an additional benefit for the isolation of anaerobes in the presence of *P. mirabilis*.

D. Observations on the Effect of Azide Concentration on Broth Cultures

The inventors next set out to determine the range of azide concentrations that are effective in anaerobic broth culture. Brain Heart Infusion (BHI) broth medium was prepared by adding azide at different concentrations. Oxygen scavenging membrane fragments, i.e. Oxyrase® for Broth, was added to each tube prior to inoculation to reduce the environment and to create and maintain an anaerobic environment. Stock cultures were diluted 1:10 and 0.1 ml and were inoculated into sterile, 5.0 ml, BHI broth in tubes. In the case of *F. nucleatum* and *P. anaerobius*, the stock culture was not diluted before inoculation and 0.5 ml was inoculated into the BHI tube. The tubes were incubated for 48 hours at 37° C. before the following observations were made (See Table 4).

TABLE 4

Effect of Azide Concentration of Broth Cultures

| | Azide Concentration | | | |
|---|---|---|---|---|
| Culture | 0 mg/ml | 0.01 mg/ml | 0.02 mg/ml | 0.04 mg/ml |
| Anaerobe microbes | | | | |
| *Bacteriodes fragilis* | + + + + | + + + + | + + + + | + + + |
| *Clostridium perfringens* | + + + + | + + + + | + + + + | + + + + |
| *Fusobacterium nucleatum* | − | − | − | − |
| *Porphyromonas levii* | + + + + | + + + + | + + + | + + |
| *Peptostreptococcus anaerobius* | − | − | − | − |
| Facultative microbes | | | | |
| *Escherichia coli* | + + + + | + | +/− | − |
| *Proteus mirabilis* | + + + + | + + | + | +/− |

Figure 2:
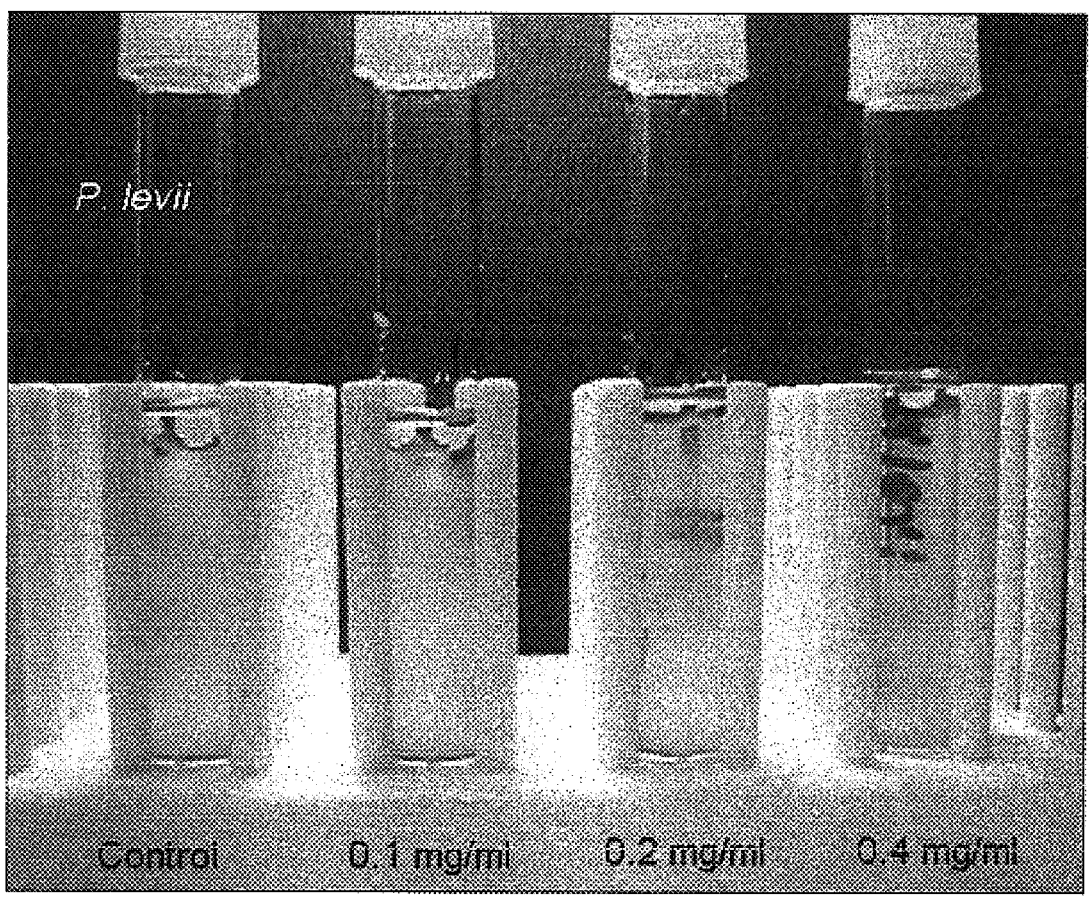
FIG. 2 is a photograph showing the growth of *P. levii* at various azide concentrations.
Figure 3:
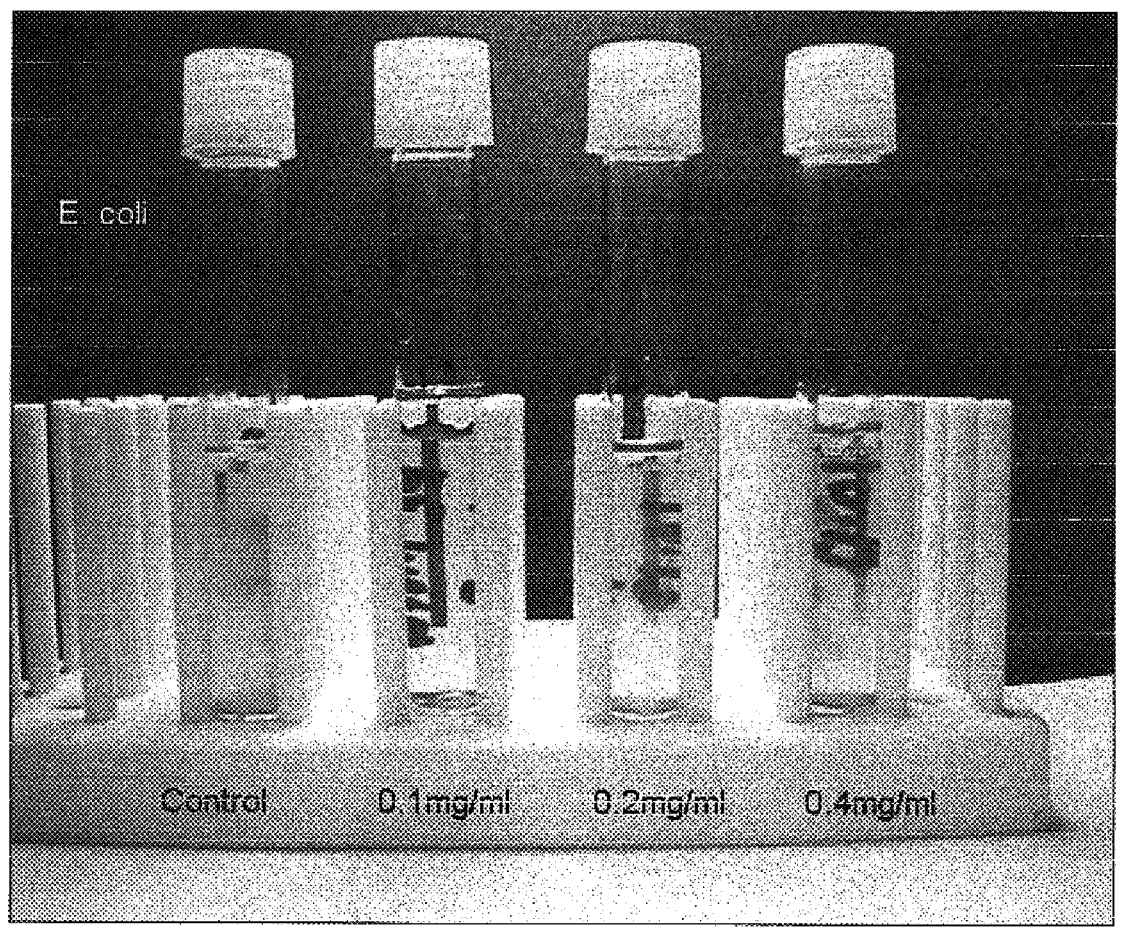
Figure 4:
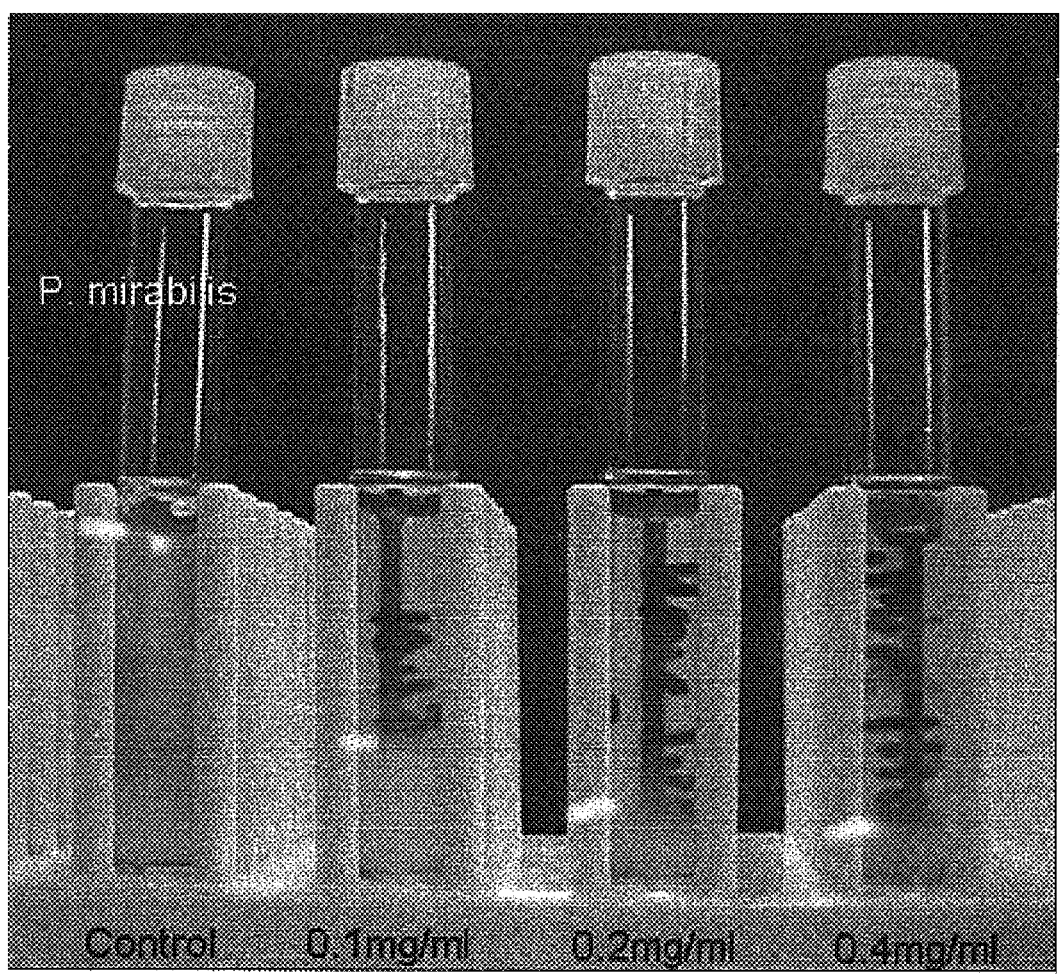

The results showed that the anaerobe microbes grow in the presence of azide whereas the facultatives are inhibited by azide under anaerobic conditions. As the concentration of azide is increased, growth of some anaerobes are slightly affected, but less than that of the facultative microbes. Photographic examples of these results are shown for *C. perfringens* (FIG. 1, note the characteristic gassing), *P. levii* (FIG. 2), *E. coli* (FIG. 3), and *P. mirabilis* (FIG. 4, the yellow markers show the level of growth in the tube).

Samples of the above cultures were plated on Brucella OxyPlate™ devoid of any azide. Even though the level of growth of *F. nucleatum* and *P. anaerobius* was below visible turbidity at 48 hours (less than $10^7$ CFU/ml), the plates had numerous colonies. Continued incubation of these cultures for up to 5 days results in visible growth. One of the facultative microbes, *Proteus mirabilis* is more tolerant of azide than is *Escherichia coli* in anoxic broth, but it is unable to grow at the higher levels of azide. Plating of the facultative microbes results in numerous colonies which shows that most cells retain viability even thought their growth is limited in anoxic broth. These results show that azide in broth and anoxia provides an advantage for the growth of the anaerobe microbe over that of the facultative microbe and that this advantage can be optimized by selecting an effective concentration of azide.

E. Comparison of OxyPlate™ Cultures with and without Azide

Figure 5:
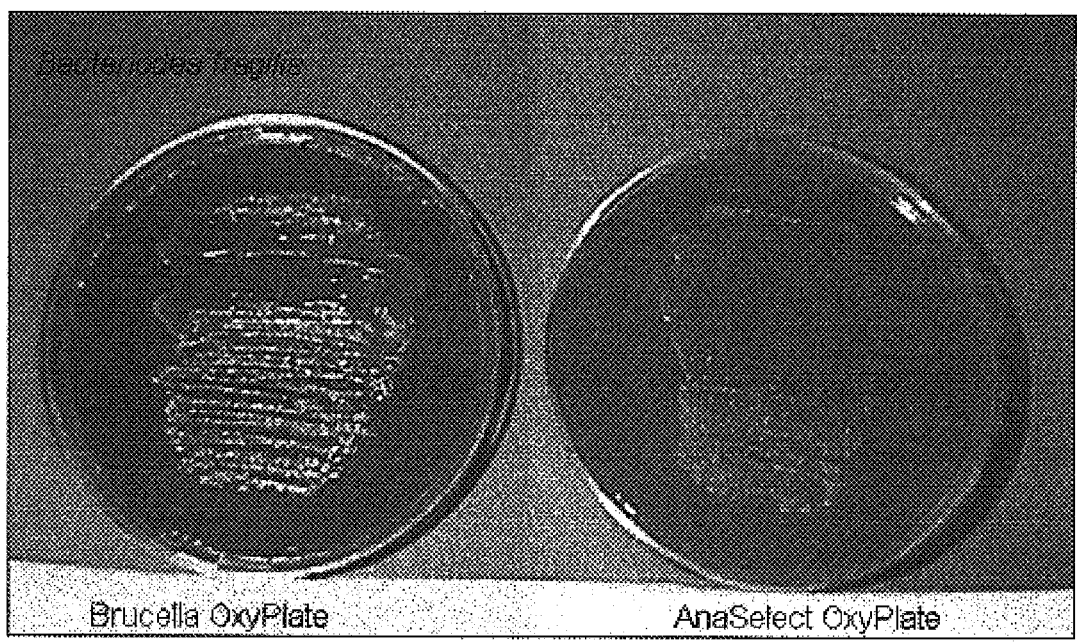
Figure 6:
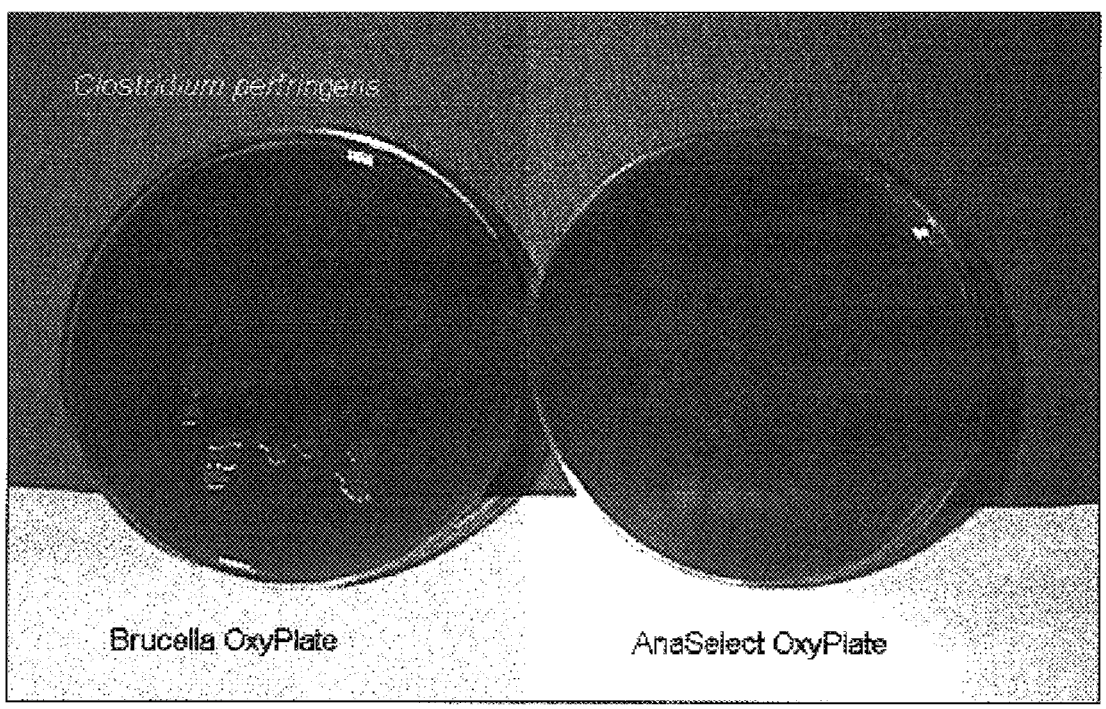
Figure 7:
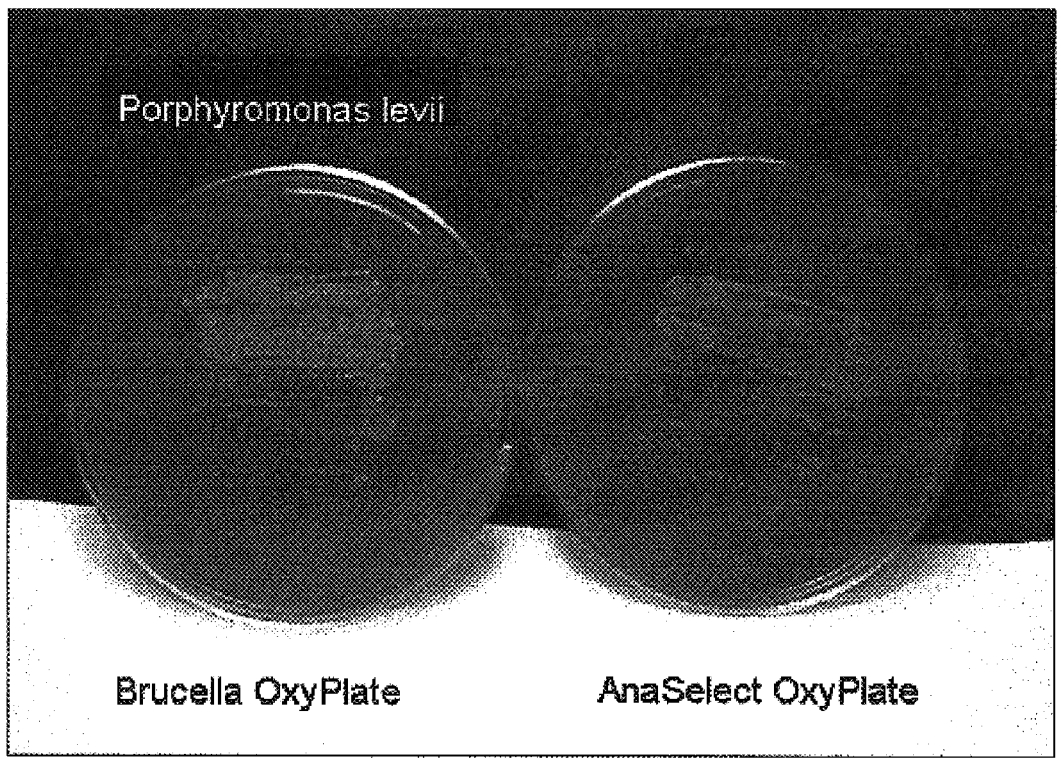
Figure 8:
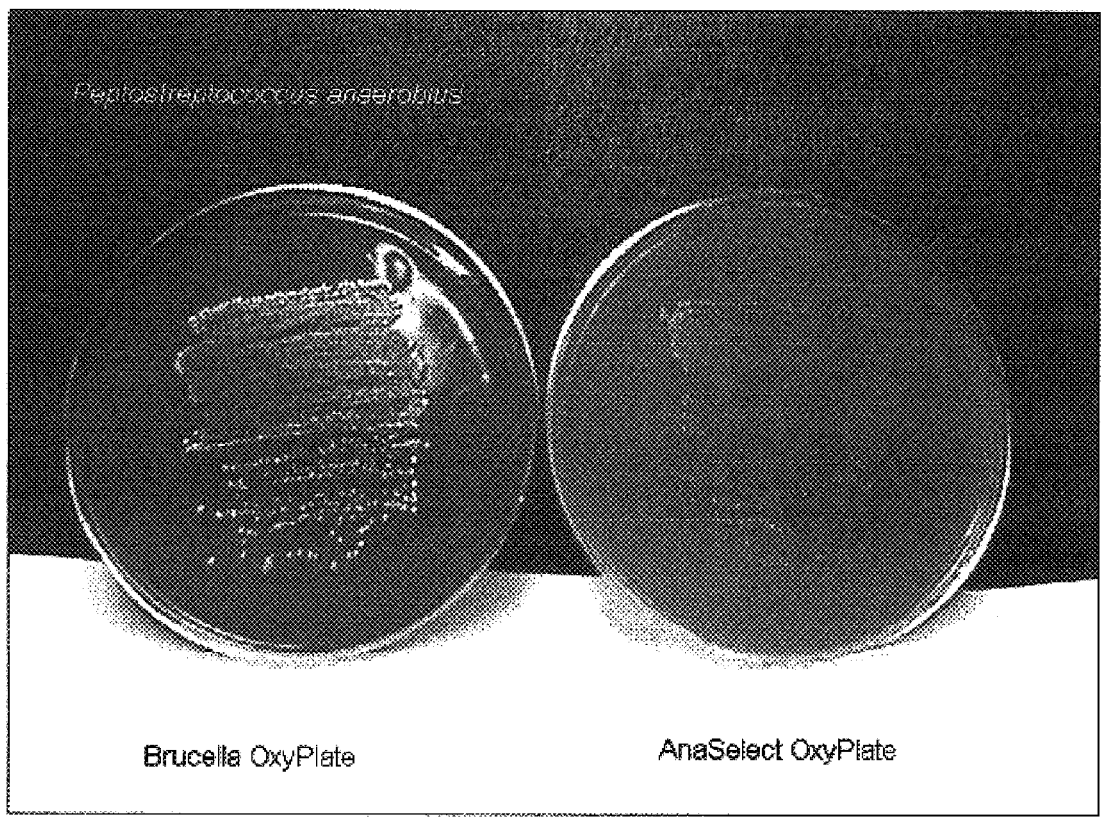
Figure 9:
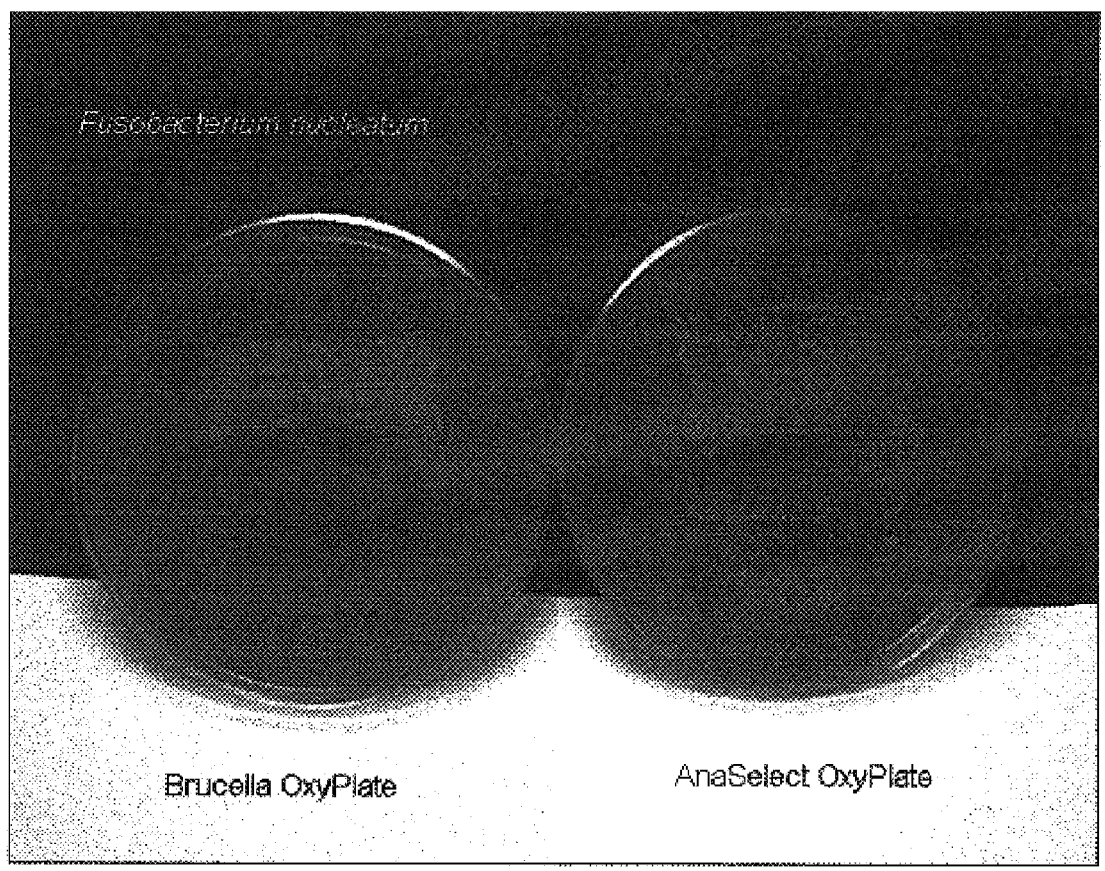
Figure 10:
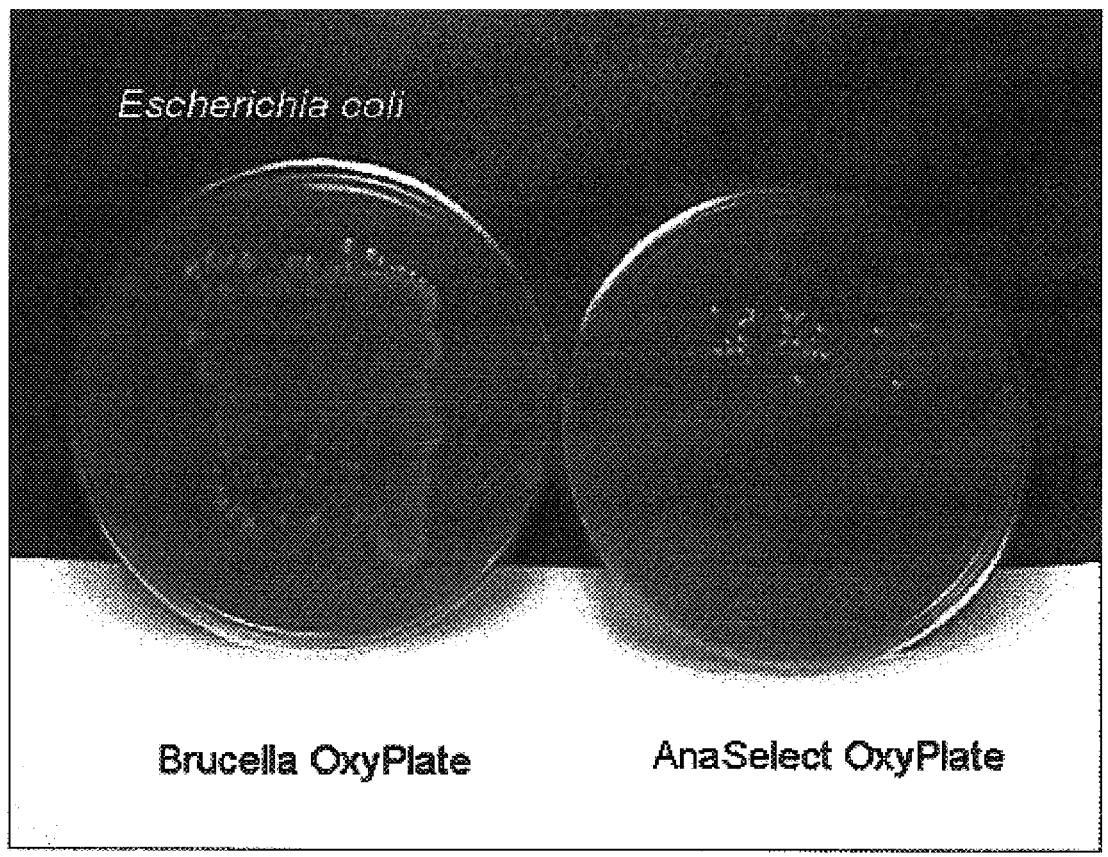

A concentration of azide (0.025 mg/ml) was chosen to make Brucella OxyPlates™. A drop of stock culture was streaked onto a control plate, lacking azide, and onto a plate containing azide, designated AnaSelect™. The plates were incubated at 37° C. for three days and the photographs taken. The results are shown for the anaerobes *B. fragilis* (FIG. 5), *C. perfringens* (FIG. 6), *P. levii* (FIG. 7), *P. anaerobius* (FIG. 8), and *F. nucleatum* (FIG. 9), and for the facultative *E. coli* (FIG. 10).

Examination of the photographs show that growth for anaerobe microbes on the azide containing plate was very similar to that on the control plate without the azide. In contrast, growth for the facultative *E. coli* on the azide containing plate under anaerobic conditions was greatly limited compared to the control plate. A similar result was observed for the facultative *P. mirabilis*, but a photograph was not available.

F. Recovery of Anaerobes from Mixed Suspensions with Facultative Microbes

The results show that growth of anaerobe microbes is unaffected by concentrations of azide that limit the growth of facultative microbes. The inventors then set out to determine if this relative difference would aid in the recovery of anaerobes in the presence of facultative microbes.

Stock cultures of the facultative microbes *E. coli* and *P. mirabilis* were adjusted to a density equivalent to a McFarland 0.5. A further 1:10 dilution was made of this adjusted suspension. The relative numbers of colony forming units in these suspensions would be in the range of $1 \times 10^8$ to $1 \times 10^7$ CFU/ml. Equal amounts of these suspensions were mixed with stock cultures of an anaerobe. The anaerobe culture would have a range of CFU like that of the diluted facultative suspension. In some cases, the anaerobe culture was diluted 1:10 before adding to the mixture.

A calibrated loop full (0.01 ml) of these suspensions was streaked onto a Brucella OxyPlate™ (control) and onto an AnaSelect™ (Brucella medium with 0.025 mg/ml of azide) OxyPlate™. The plates were incubated two or three days and photographed. The photograph is identified by the anaerobe present.

Figure 11:
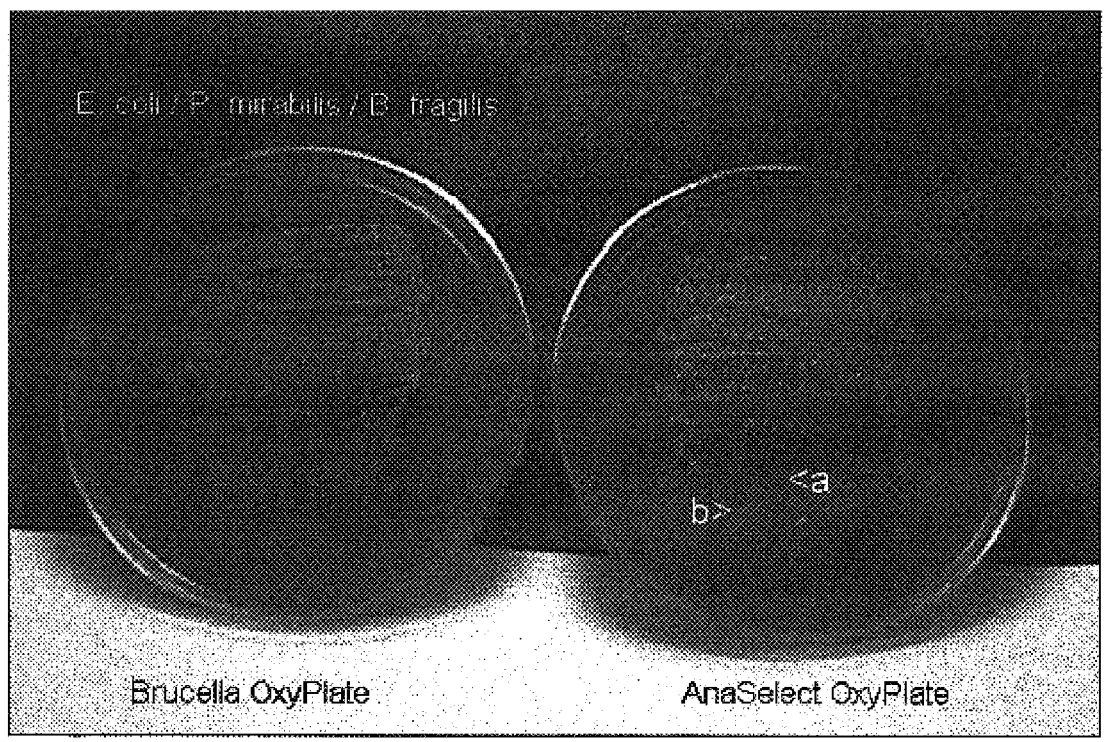

*B. fragilis* (FIG. 11): The control plate is densely covered with colonies that are those of the *E. coli* and *P. mirabilis*. It would be very difficult to identify or to pick an isolated *B. fragilis* colony from this plate. In contrast, the AnaSelect™ plate contains relatively fewer colonies of *E. coli* and *P. mirabilis* (marker b ), but does contain numerous, isolated colonies of *B. fragilis* (marker a).

Figure 12:
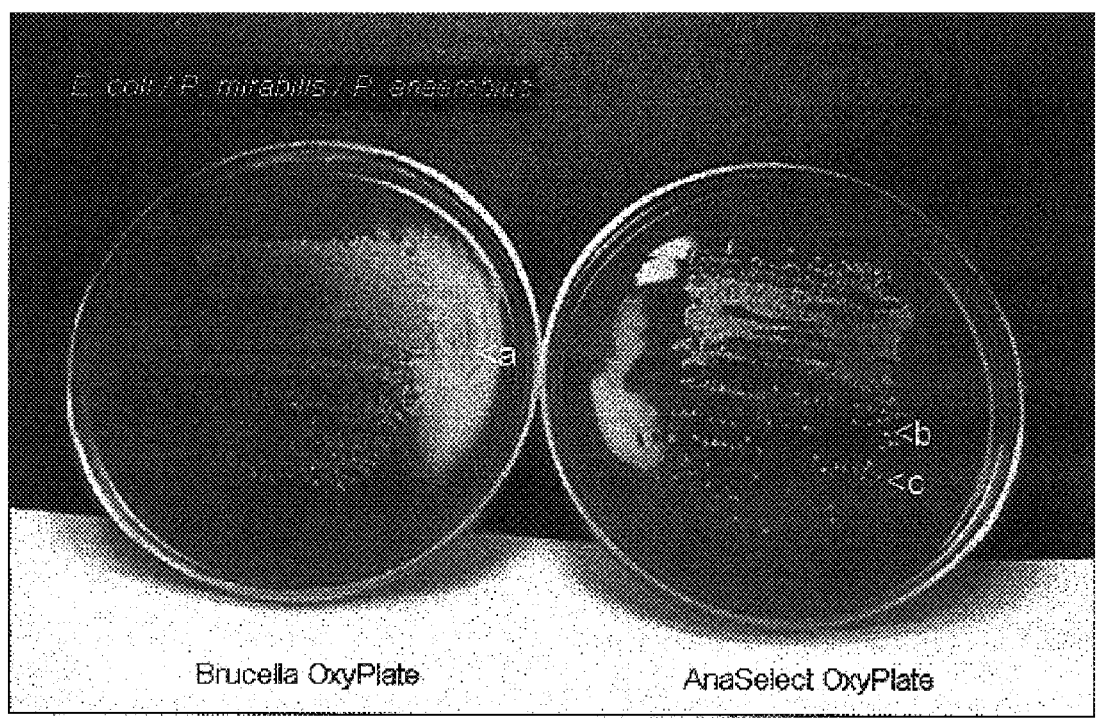

*P. anaerobius* (FIG. 12): The control plate is densely populated by the facultative microbes. Note that *P. mirabilis* is spreading over the surface of the agar (marker a). Although not clearly observable in this photograph, spreading of this microbe has occurred throughout the plate, which makes isolation of separate, single colonies difficult to impossible. One cannot find a clearly observable anaerobe on this plate. In contrast, the AnaSelect™ plate contains fewer facultative microbes. The colonies of *P. mirabilis* (marker b) are contained and not spreading on this AnaSelect™ plate. Clearly identifiable and separate colonies of the anaerobe *P. anaerobius* are readily found on this plate (marker c).

Figure 13:
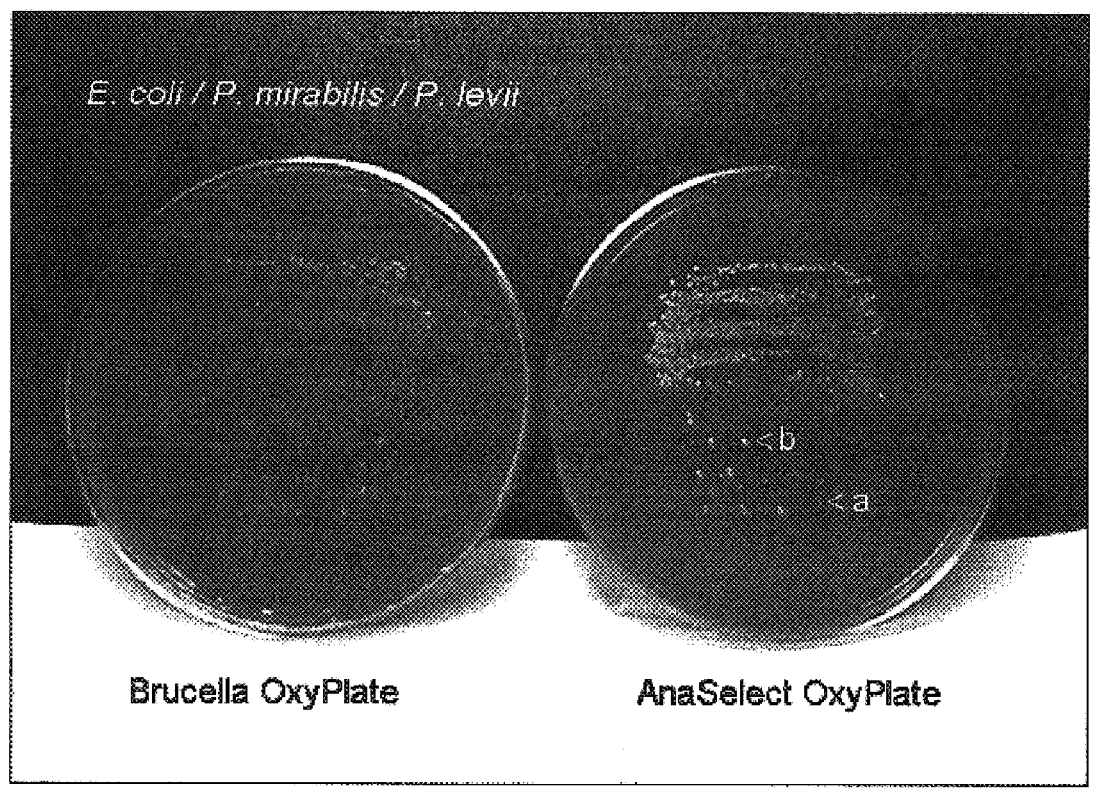

*P. levii* (FIG. 13): The same commentary applies to this photograph. Colonies of *P. mirabilis* on the AnaSelect™ plate are contained and not spreading (marker b). Well separated and identifiable colonies of the *P. levii* are shown on the AnaSelect™ plate (marker a).

Figure 14:
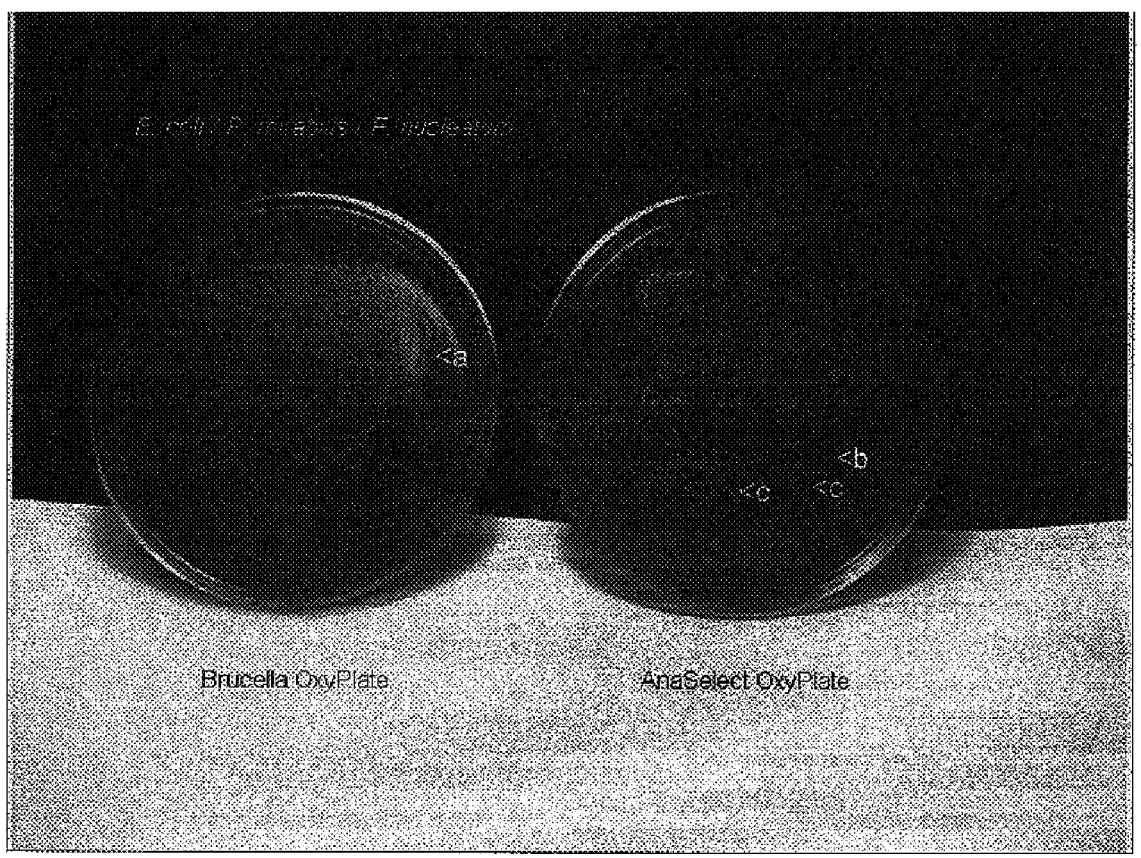

*F. nucleatum* (FIG. 14): The same commentary applies to this photograph. Note the swarming of *P. mirabilis* (marker a) on the control plate and the contained, nonspreading colonies on the AnaSelect™ plate (marker b). The target anaerobe, *F. nucleatum* is readily observable on the AnaSelect™ plate (marker c).

Figure 15:
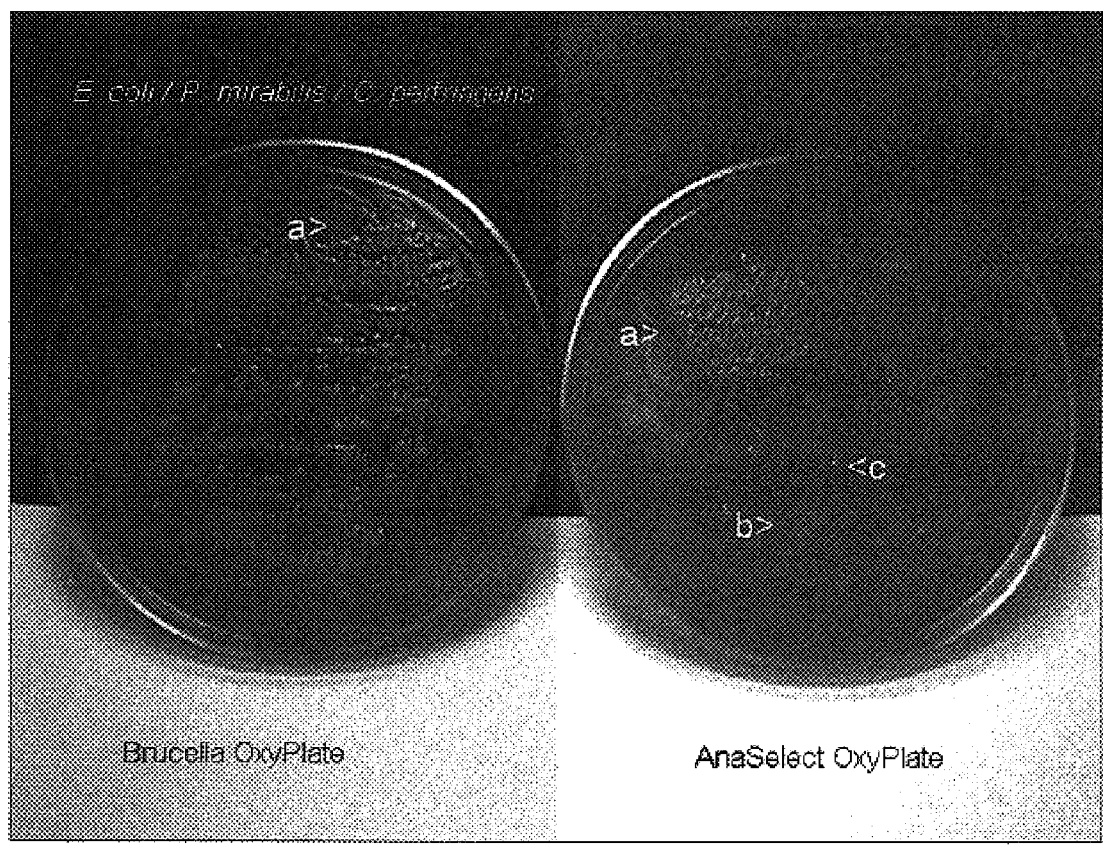

*C. perfringens* (FIG. 15): The interaction of *P. mirabilis* and *C. perfringens* creates a different situation. *P. mirabilis* actively swarms on the control plate and on the AnaSelect™ plate (marker a). Swarming on the control plate is extensive, whereas, swarming on the AnaSelect™ plate is limited to that portion of the streak that is most dense with microorganisms (top of plate). Note that when single colonies are observable, *P. mirabilis* does not swarm (marker c). On this portion of the plate (bottom) readily identifiable and separate colonies of *C. perfringens* are found (marker b).

These results clearly show that under anoxic conditions plates containing azide have a very practical application for separating and isolating anaerobe microbes from mixtures containing superior numbers of facultative microbes. This can not be done on anoxic plates without azide.

G. Method for Rapidly Recognizing, Isolating, and Identifying Anaerobe Microbe in Mixed Culture with Facultative Microbe Currently, mixed broth cultures heavily favor the growth of facultative microbes. Anaerobes are diluted to extinction by growth of facultative microbes. Isolation of anaerobes from mixed broth cultures fails for this reason. The ability of azide to preferentially favor the growth of an anaerobe microbe over that of a facultative microbe in anoxic broth creates an opportunity to develop a method whereby an anaerobe can be selectively isolated from a mixed broth culture containing facultative microbes. There are many situations where samples contain a mixture of anaerobe and facultative microbes (clinical labs, food samples, environmental samples). Broth culture has advantages over plate culture for growing anaerobes. An anoxic environment can be created and maintained in broth more readily than in plate culture (at less cost also). Anaerobe cells can be transferred from a sample to broth with minimal exposure to air, thereby limiting detrimental affect of exposure to oxygen for fastidious anaerobes. Detection of growth is often quicker in broth than on plates. Once obtained, cells in broth are easily manipulated.

For these reasons the inventors set out to develop a method using broth culture as the primary step for the detection, identification, and isolation of anaerobes from a mixed culture containing facultative microbes. The first step is the selective enhancement of the anaerobe at the expense of the facultative microbe by cultivation in anoxic broth containing oxygen scavenging membrane fragments and azide. At this point sufficient enrichment has occurred to make identification possible through microscopic observation of a gram stain and or through use of DNA probes, RNA probes, or specific antibodies. Purification of the anaerobe microbe is accomplished by the second step of plating the broth culture onto a plate containing azide and incubating that plate anaerobically. The combination of broth enrichment and isolation on a plate, under the selective affects of azide and anoxic growth, provide a powerful method to obtain the anaerobe from a mixed culture.

A mixed suspension of E. coli, P. mirabilis, and the target anaerobe were made by combining 1 part of each. Stock cultures E. coli and P. mirabilis were first adjusted to a cell density equivalent to a 0.5 McFarland of which a 1:10 dilution was made. The stock cultures of the target anaerobes were diluted 1:10 before being added to the mix, except for B. fragilis, which was diluted 1:100. The objective is to have a majority of cells in the mix being facultative microbes.

To tubes containing 5.0 ml of BHI broth were added Oxyrase® for Broth (1 drop per ml of medium) which creates and maintains an anaerobic environment. Sets of tubes were made to 0.1 mg/ml, 0.2 mg/ml and 0.4 mg/ml with sodium azide.

Each tube was inoculated with 0.1 ml of the mixed suspension of microbes. The broth was overlaid with sterile mineral oil to assure anaerobic conditions during incubation. The inoculated tubes were incubated at 37° C. for 48 hours.

Observations: Control tubes, not containing azide, were heavily turbid throughout the broth from the bottom of the tube to the top of the broth. Tubes containing azide had varying degrees of turbidity starting at the bottom of the tube and extending upward, but not to the top of the broth. Generally, growth in the azide containing tube was greater at the lowest concentration of azide and less as the concentration of azide increased. Growth of the mixed cells was limited (selective) in the tubes containing azide.

The tubes were mixed and a sample streaked onto blood agar OxyPlates™, one containing 0.025 mg/ml azide. The plate without azide is identified as Control. The plate containing azide is identified as AnaSelect™. The plates were incubated at 37° C. for three days before observation.

Observations: A narrative of what was observed for each mixed culture set follows. The culture is identified by the target anaerobe microbe that was added to the mix. Only the observations from the culture tube containing the azide are recorded below. The tube containing the lowest concentration of azide that successfully separated the anaerobe was reported below. The results from the culture tube not containing azide were uniformly the same. The colonies on the plates were E. coli and P. mirabilis and the P. mirabilis swarmed on the agar surface. One could not recognize identifiable anaerobe colonies on these plates.

B. fragills: (0.2 mg/ml) Control: Numerous colonies. Distinguishable anaerobe colonies not observable. AnaSelect™: Recognizable and separated B. fragilis colonies in abundance. P. mirabilis colonies present, but no swarming.

C. perfringens: (0.1 mg/ml) Control: A few recognizable C. perfringens colonies among numerous colonies of E. coli and P. mirabilis, which swarmed. AnaSelect™: Numerous, well isolate C. perfringens colonies obtained. P. mirabilis swarmed in the densely growing region of the streak.

P. levii: (0.1 mg/ml) Control: Mix of colony types. P. mirabilis swarmed. Anaerobe not recognizable. AnaSelect™: Mixed colonies. Recognizable and separated colonies of P. levii obtained. P. mirabilis not swarmed.

P. anaerobius: (0.1 mg/ml) Control: Mix of colony types. Anaerobe not recognizable. AnaSelect™: Fewer colonies, many of which are P. anaerobius.

F. nucleatum: (0.1 mg/ml) Control: Mix of colony types. P. mirabilis swarmed. Anaerobe not clearly recognizable. AnaSelect™: Fewer colonies. P. mirabilis not swarmed. Few colonies that appear to be F. nucleatum (not confirmed).

Several conclusions can be drawn from this experiment:
1. Mixed cultures of facultative microbes with anaerobe microbes grown in broth anaerobically under non-selective conditions yield overwhelmingly facultative microbes. Anaerobes are impossible to identify on plates inoculated with these cultures.
2. Mixed cultures of facultative microbes with anaerobe microbes grown in broth anaerobically with azide yield isolated, identifiable colonies of the target anaerobe. It is apparent by observation that growth in these cultures is selective, that is turbidity is lower than in the control and is limited to the lower half of the broth column. From other experiments, the inventors knew that the growth of anaerobe microbes is unaffected by azide; whereas, growth of facultative microbes is limited by azide.
3. The facultative microbes put into the selective environment of azide and anoxia is at a growth disadvantage relative to the anaerobe microbe, but the facultative microbes retain viability as observed when these cultures are inoculated onto an anaerobically incubated, non-selective medium (Control in above Observations). Growth of the anaerobe microbe in broth under the favorable, select conditions with azide amplify their number, but under the conditions of this experiment where the initial number of facultative microbes are very high, isolation and separation of the anaerobe is not readily doable on a non-selective plate.
4. The power of the AnaSelect™ Method, that uses a combination of selective broth cultivation followed by plating on a selective plate, is clearly demonstrated in this example. In each case, it was possible to further limit the numbers of facultative microbes and to contain the spreading of P. mirabilis by plating the selected broth culture on a selective plate. In four out of five examples, clearly identifiable and separated colonies of the target anaerobe were obtained by this method. In the fifth example for F. nucleatum, the colonies were like those of F. nucleatum but they were not confirmed to be F. nucleatum.

H. Use of AnaSelect™ Method with Clinical Specimens

A common routine in the clinical laboratory is to inoculate a specimen onto blood agar media. If an anaerobe is suspected then two plates are inoculated. One plate is incubated aerobically and the other is incubated anaerobically. These are called primary plates. The plates are used to isolate the microbes present in the specimen as individual colonies. The morphological characteristics of the colonies helps to identify the kind of microbe present. The aerobically incubated plate and the anaerobically incubated plate are compared. The presence of a colony type on the anaerobically incubated plate that is not present on the aerobically incubated plate is presumptive evidence that an anaerobe microbe is present.

Concurrently with planting the primary plates, the specimen is inoculated into a broth medium, usually Thioglycollate broth, as a "back up" to the primary plates. If an anaerobe is suspected, then two tubes are inoculated. One tube is incubated aerobically and the other anaerobically. Often the broth cultures are only used if a primary plate failed or a suspected microbe was not isolated. Then the broth culture would be plated onto blood agar plates as done for the primary isolation procedure and the resulting colonies studied.

In some clinical laboratories use of Thioglycollate broth tubes as a back up to primary plates is discontinued because the results are not useful. Anaerobe microorganisms are infrequently recovered from the broth tubes. The facultative microbes, often found in mixed infections, out grow the anaerobes present. It is this situation that AnaSelect™ was designed to correct, namely to prevent or retard the growth of facultative microbes while allowing any anaerobe microbes present to grow.

The purpose of the AnaSelect™ trial in the clinical laboratory was to determine that the results obtained in the laboratory would be replicated with specimens that contain mixed populations of microbes of unknown and uncontrolled composition.

I. Comparison of AnaSelect™ Thioglycollate Broth Tubes to Standard Thioglycollate Tubes AnaSelect™ Thioglycollate broth tubes contained the poison sodium azide as describe in this invention. They were made by adding oxygen scavenging enzyme fragments, i.e. Oxyrase® for Broth, containing sodium azide to Thioglycollate broth medium. These tubes were included in the routine procedure for analyzing patient specimens in a clinical laboratory. Thioglycollate tubes containing Oxyrase® for Broth were incubated aerobically because the Oxyrase® creates and maintains an anaerobic environment within the tubes. The same specimens were inoculated into Thioglycollate broth and incubated in an anaerobic environment, as is the standard practice in this laboratory.

Twenty five specimens were processed. The tubes were incubated at 35° C. to 37° C. for 48 hours. A sample was taken from the Standard Thio tube and from the AnaSelect™ Thio tube and streaked onto blood agar plates. Thirteen of the twenty five tube pairs were exactly the same and not reported. Eleven of the tube pairs were different from each other and the results are reported in Table 5.

TABLE 5

Results Comparing Standard Thioglycollate to Oxyrase AnaSelect ™ Thioglycollate

| | Standard Thio | AnaSelect ™ Thio |
|---|---|---|
| 1 | Gram neg rod (aerobic) | negative |
| 2 | Staphylococcus | negative |
| 3 | Staphylococcus | negative |
| 4 | Staphylococcus/Diptheroid | Diptheroid |
| 5 | Gram neg rod (aerobic) | P. magnus |
| 6 | Staphylococcus | negative |
| 7 | Gram pos cocci; Gram neg rods; Gram pos rods (aerobes) | Staphylococcus |
| 8 | Staphylococcus | negative |
| 9 | Yeast | negative |
| 10 | Staphylococcus | Peptostreptococcus sp |
| 11 | Staphylococcus | negative |

Observations

44% of the Thio tubes from randomly chosen patient specimens differed. Among those that differed, anaerobes were found in two of the AnaSelec™ Thio tubes (#5 and #10); whereas, no anaerobes were found in the Standard Thio tubes. The plates from Standard tubes #5 and #10 showed growth of aerobe and facultative microbes that were not reported on the plates from the same specimens from the AnaSelect™ tubes.

Seven of the eleven AnaSelec™ tubes were reported as negative (no growth) on plates; whereas, the corresponding Standard Thio tubes reported growth of aerobic or facultative microbes. Of the two AnaSelect™ tubes that yielded growth of facultative microbes (#4 and #7), the number and kinds of facultative microbes in the corresponding Standard tubes were greater.

Interpretation of Results:

This comparison of Standard Thio tubes and AnaSelec™ Thio tubes from randomly chosen patient specimens is in complete agreement with the controlled laboratory experiments using mixed cultures reported before. The clinical evaluation demonstrate the practical value that AnaSelec™ brings to isolating anaerobes from patient specimens. This evaluation supports the conclusions that:

1. In Standard Thio broth inoculated with clinical specimens, facultative microbes out grow anaerobes.
2. In AnaSelect™ Thio broth inoculated with clinical specimens, growth of facultative microbes is discouraged.
3. Anaerobes were isolated from AnaSelect™ Thio but not Standard Thio tubes inoculated with clinical specimens.

J. Comparison of Isolates from AnaSelect™ Thio Tubes to Isolates from Primary Plates A second evaluation was done using AnaSelect™ Thio tubes inoculated with patient specimens. The tubes were incubated 48 hours at 35° C. to 37° C. before plating on blood agar plates. Of 40 patient specimens, 12 were positive for anaerobes on either the primary plate, the plate from the AnaSelect™ Thio tube, or both. Of those positive specimens, the kind of anaerobes found on the primary plate and the plates from the AnaSelect™ Thio tube were compared. The results are reported in Table 6.

TABLE 6

Comparison of Isolates on Primary Plates to Plates from AnaSelect ™ Thio

| | Isolates from Primary Plate | Isolates from AnaSelect ™ Thio |
|---|---|---|
| 1 | Fusobacterium, P magnus | data lost |
| 2 | P. magnus | P. magnus |
| 3 | negative | Peptostreptococcus sp. |
| 4 | P. micros | P. micros |
| 5 | P. micros | P. micros |
| 6 | negative | Lactobacillus sp. |
| 7 | P. micros | negative |
| 8 | Bacteriodes sp, Fusobacterium | Peptostreptococcus, P. magnus, Bacteriodes sp. |
| 9 | P. magnus | negative |
| 10 | P. magnus | negative |
| 11 | negative | P. magnus |
| 12 | Peptostreptococcus sp. | Peptostreptococcus sp. |

Observations

1. In three of the 12 positive specimens anaerobes were found on the plates from the AnaSelect™ Thio tube that were not found on the primary plates (#3, #6, and #11).
2. In three of the 12 positive specimens anaerobes were found on the primary plates that were not found on the plates from the corresponding AnaSelect Thio tubes (#7, #9, and #10).
3. In one specimen (#8), different anaerobes were found on the primary plate than what was found on the plate from the comparable AnaSelect™ tube.

Interpretation of Results

These results show that the AnaSelect™ Method is equivalent to primary plates for the detection and isolation of anaerobes from patient specimens. The results suggest that the combination of primary plates and the AnaSelect™ Method detects more anaerobes than either one alone.

K. Comparison of Isolates from Primary Plates to Isolates from Plates from AnaSelec™ Thio This evaluation was a repeat of the 2$^{nd}$ evaluation with a difference being the AnaSelect™ Thio tube was incubated 72 hours at 35° C. to 37° C. instead of 48 hours. Some fastidious anaerobe microbes grow slowly. In some specimens the number of anaerobes inoculated into the tube may be low. This incubation time modification was done to learn if there was any affect on the kinds and numbers of anaerobes recovered in the AnaSelect™ Thio tube. Of 36 specimens tested, 14 were positive for anaerobes. The results are presented in Table 7.

TABLE 7

Comparison of Isolates on Primary Plates to Plates from AnaSelect ™ Thio

| | Primary Plates | AnaSelect ™ Thio Plates |
|---|---|---|
| 1 | P. magnus, Peptostreptococcus sp | P. magnus, Peptostreptococcus sp |
| 2 | P. magnus, Bacteroides sp., Prevotella | P magnus, Bacteroides sp., Prevotella |
| 3 | P. magnus | P. magnus |
| 4 | P. magnus | P. magnus |
| 5 | B. fragilis grp | B. fragilis grp |
| 6 | negative | P. magnus |
| 7 | Bacterioides sp, Fuso sp., P. magnus | Staphl. Fuso sp. |
| 8 | P. magnus | P. magnus, Anaerobe Gram neg rod |
| 9 | Bacteroides sp. | data not recorded |
| 10 | P. magnus | P. magnus |
| 11 | Peptostreptococcus sp | Peptostreptococcus sp |
| 12 | P. magnus, Prevotella | P. magnus, Prevotella |
| 13 | P. magnus | P. magnus |
| 14 | Anaerobe Gram pos rod, Prevotella | Anaerobe Gram pos rod, Prevotella |

Observations
1. In 10 out of 14 positive specimens, the number and kind of anaerobes found on the primary plate and on the plate from the AnaSelect™ Thio tube were the same.
2. In one specimen (#6), an anaerobe was found on the AnaSelect™ Thio plate that was not found on the primary plate.
3. In two specimens (#7 and #8) the anaerobes found on the primary plate and the AnaSelect™ plate were not the same. For specimen #7, the number of anaerobes found on the primary plate was greater than on the AnaSelect™ Thio plate; whereas, the reverse result was found for specimen #8.

Interpretation

The results from the third trial supports the conclusion that the AnaSelect™ Method is equivalent to primary plates for finding anaerobes in clinical specimens. The data again suggests that the combination of primary plates and the AnaSelect™ Method yields more anaerobes than either method alone. There was no evidence to indicate that longer incubation of the AnaSelect™ Thio tube increased the recovery of anaerobes from patient specimens.

CONCLUSION

These trials with random, clinical specimens support and reinforce the data from controlled experiments. They confer a higher standard because clinical patient specimens are the ultimate test for the AnaSelect™ Method. Clinical specimens contain variable number and kinds of facultative and anaerobe microbes. This work was carried out amid the flow of processing patient specimens in a hospital laboratory by several different technicians. The results demonstrate the efficacy of the AnaSelect™ Method for finding anaerobes in mixed infections.

Some additional conclusions supported by these clinical trials:
1. Standard Thio cultures are not reliable for obtaining anaerobes from mixed infection because the facultative microbes out grow the anaerobes.
2. AnaSelect™ Thio broth cultures yield fewer facultative microbes than Standard Thio broth cultures, which accounts for the successful isolation of anaerobes from AnaSelect™ broth cultures.
3. The number and kind of anaerobes obtained from AnaSelect™ Thio broth cultures are equivalent to those found on primary plates. This supports the conclusion that AnaSelect™ allows the growth of anaerobes indiscriminately, while limiting the growth of facultative microbes.
4. The combination of the AnaSelect™ Method with primary plates yields more anaerobes than either method alone.

The invention has been described with reference to the preferred embodiments. Obviously, modifications and alterations will occur to others upon reading and understanding the preceding detailed description. It is intended that the invention be construed as including all such alterations and modifications insofar as they come within the scope of the claims and the equivalents thereof.

Having thus described the preferred embodiments, the invention is now claimed to be:

1. An anaerobic medium composition for the selective growth of anaerobes from a sample that contains at least facultative microorganisms and anaerobes, wherein said medium composition comprises a nutrient medium, a salt of an azide present in an amount of from about 0.1 mg/ml to 1.0 mg/ml in the medium, and oxygen scavenging membrane fragments to create an anaerobic environment, wherein the membrane fragments are derived from a respiratory system of an organism sensitive to azide.

2. The medium composition of claim 1, wherein the medium comprises Brain Heart Infusion, Brucella, CDC Anaerobe, Nutrient, Schaedler, Thioglycollate, or Trypticase Soy.

3. The medium composition of claim 1, wherein the sample is obtained from
 a. patients;
 b. economically important animals; or
 c. pharmaceutical, or environmental sources.

4. A method for the rapid recognition, isolation, or identification of anaerobes from a sample that contains at least facultative microorganisms and anaerobes comprising the following steps:
 a. providing a liquid medium composition comprising a nutrient medium and a salt of an azide, wherein the azide is present in an amount of from about 0.1 mg/ml to 1.0 mg/ml in the medium, and oxygen scavenging membrane fragments to create an anaerobic environment, wherein the membrane fragments are derived from the respiratory system of an organism sensitive to azide;
 b. inoculating the sample into the liquid medium composition;
 c. incubating the inoculated liquid medium composition;

d. determining the presence of growth in the inoculated liquid medium composition, with partial growth being indicative that an anaerobe is present; and, e. sampling the inoculated liquid medium composition for further characterization and isolation of the anaerobe organism.

5. A device for the transport of a sample that contains anaerobes and facultative microbes to enable the recovery of the anaerobes, wherein the device comprises the self-generating anaerobic medium composition of claim 1.

6. A medium composition which allows for the selective growth of an anaerobe contained in a mixed sample also containing at least a facultative microbe comprising: a microbiological nutrient medium containing a hydrogen donating substance, a plurality of oxygen scavenging membrane fragments which contain an electron transport system which reduces oxygen to water in the presence of a hydrogen donor, and an inhibitor of the electron transport system required for cellular respiration, wherein the inhibitor is present in an amount of from about 0.1 mg/ml to 1.0 mg/ml in the medium, and wherein the oxygen scavenging membrane fragments are derived from respiring bacteria.

7. The medium composition of claim 6, wherein the hydrogen donating substance comprises an organic substrate.

8. The medium composition of claim 6, wherein the hydrogen donating substance comprises lactic acid, succinic acid, alpha-glycerol phosphate, formic acid or malic acid or any of their corresponding salts.

9. The medium composition of claim 6, wherein the oxygen scavenging membrane fragments are derived from the cytoplasmic membranes of *Escherichia coli*.

10. The medium composition of claim 6, wherein the inhibitor of the electron transport system comprises an azide or cyanide.

11. The medium composition of claim 6, wherein the inhibitor of the electron transport system comprises a salt of an azide or a cyanide.

12. The medium composition of claim 6, wherein the inhibitor of the electron transport system is sodium azide.

13. The medium composition of claim 6, wherein the microbiological nutrient medium comprises Brain Heart Infusion, Brucella, CDC Anaerobe, Nutrient, Schaedler, Thioglycollate or Trypticase Soy medium in broth or agar form.

14. A medium composition which restricts the growth of facultative microbes but not anaerobic microbes comprising a nutrient medium comprising a hydrogen donating organic substrate, one or more oxygen scavenging membrane fragments derived from the cytoplasmic membranes of bacteria, and an inhibitor of the electron transport system required for aerobic respiration in an amount of from about 0.1 mg/ml to 1.0 mg/ml in the medium.

15. The medium composition of claim 14, wherein the oxygen scavenging membrane fragments are derived from the cytoplasmic membranes of *Escherichia coli*.

16. The medium composition of claim 14, wherein the inhibitor of the electron transport system comprises a salt of azide or cyanide.

17. The medium composition of claim 14, wherein the inhibitor is sodium azide.

18. A medium composition which restricts the exponential growth of facultative microbes but not anaerobic microbes comprising a base medium containing a hydrogen donating substrate, oxygen scavenging membrane fragments derived from the cytoplasmic membranes of *Escherichia coli*, and a salt of an azide in an amount of about 0.1 mg/ml to 1.0 mg/ml in the medium.

19. A method for the selective growth of an anaerobe from a sample containing a facultative microbe, said method comprising the steps of:

a. providing a medium composition comprising a nutrient medium containing a hydrogen donating substance, a salt of an azide in an amount of from about 0.1 mg/ml to 1.0 mg/ml in the nutrient medium, and oxygen scavenging membrane fragments which contain an electron transport system which reduces oxygen to water in the presence of a hydrogen donor, wherein the membrane fragments are derived from the respiratory system of an organism normally sensitive to azide;

b. inoculating the medium composition with the sample; and, c. incubating the medium composition containing the sample.

20. A method for the selective growth of an anaerobe from a sample containing a facultative microbe, said method comprising the steps of:

a. providing an agar plate comprising a nutrient medium, a salt of an azide in an amount of from about 0.1 mg/ml to 1.0 mg/ml in the agar plate nutrient medium, and oxygen scavenging membrane fragments which reduce oxygen to water wherein the membrane fragments are derived from a respiratory system of an organism normally sensitive to azide;

b. providing a liquid broth comprising a nutrient medium and a salt of an azide in an amount of from about 0.1 mg/ml to 1.0 mg/ml in the liquid broth nutrient medium;

c. inoculating the liquid broth with the sample and thereafter incubating the inoculated broth;

d. inoculating the plated agar medium with the liquid broth containing the sample; and, e. incubating the plated agar medium inoculated with the liquid broth under anaerobic conditions thereby producing isolated colonies of the anaerobe free of facultative microbe.

21. The method of claim 20, further comprising the step of:

f. selecting isolated colonies of the anaerobes for characterization and identification.

22. A method for the selective enhancement of an anaerobe from a mixed sample also containing a facultative microorganism, said method comprising the steps of:

a. providing a liquid nutrient medium composition containing a biocatalytic oxygen reducing agent and a salt of an azide in an amount of from about 0.1 mg/ml to 1.0 mg/ml in the liquid nutrient medium composition;

b. providing an agar plate comprising a nutrient medium, a salt of an azide in an amount of from about 0.1 mg/ml to 1.0 mg/ml in the agar plate nutrient medium, a biocatalytic oxygen reducing agent, and a hydrogen donating substance;

c. inoculating the liquid medium composition with the mixed sample and thereafter incubating the inoculated broth;

d. inoculating the agar plate with the liquid medium composition containing the mixed sample; and e. incubating the agar plate containing the mixed sample under anaerobic conditions.

23. The method of claim 22, wherein the biocatalytic oxygen reducing agent comprises oxygen scavenging membrane fragments of bacteria normally sensitive to azide.

24. The method of claim 22, wherein the biocatalytic oxygen reducing agent comprises oxygen scavenging membrane fragments of mitochondrial organelles.

25. The method of claim 23, wherein the bacteria is *Escherichia coli*.

26. The method of claim 22, wherein the salt of an azide is sodium azide.

* * * * *